(12) United States Patent
Navarro et al.

(10) Patent No.: US 7,780,666 B1
(45) Date of Patent: *Aug. 24, 2010

(54) FIXED AND VARIABLE LOCKING FIXATION ASSEMBLY

(75) Inventors: Richard R. Navarro, Strongsville, OH (US); Dennis M. Madigan, Doylestown, OH (US); Morton B. Albert, Akron, OH (US); Randall R. Theken, Coventry Township, OH (US)

(73) Assignee: Theken Spine, LLC, Akron, OH (US)

( * ) Notice: Subject to any disclaimer, the term of this patent is extended or adjusted under 35 U.S.C. 154(b) by 1187 days.

This patent is subject to a terminal disclaimer.

(21) Appl. No.: 11/142,702

(22) Filed: Jun. 1, 2005
(Under 37 CFR 1.47)

Related U.S. Application Data

(62) Division of application No. 10/190,257, filed on Jul. 5, 2002, now Pat. No. 7,001,389.

(51) Int. Cl.
*A61B 17/70* (2006.01)
(52) U.S. Cl. .......................... 606/71; 606/281; 606/286
(58) Field of Classification Search .................. 606/71, 606/70, 73, 61, 69, 54, 281, 286; 411/353, 411/105
See application file for complete search history.

(56) References Cited

U.S. PATENT DOCUMENTS

| 367,011 A | 7/1887 | Rogers |
| 438,754 A | 10/1890 | Rogers |
| 824,867 A | 3/1906 | Houghton |
| 1,105,105 A | 7/1914 | Sherman |
| 1,172,825 A | 2/1916 | Oldboyd |

(Continued)

FOREIGN PATENT DOCUMENTS

AU 199655397 10/1996

(Continued)

OTHER PUBLICATIONS

R. Ashman et al., Biomechanical Analysis of Pedicle Screw Instrumentation Systems in a Corpectomy Model, Spine, 1989, 1398-1405, vol. 14, U.S.A.

(Continued)

*Primary Examiner*—Pedro Philogene
(74) *Attorney, Agent, or Firm*—Middleton Reutlinger; Robert H. Eichenberger; Eric L. Killmeier

(57) ABSTRACT

A locking screw assembly is provided which allows installation into a plate-like member using relatively little force, but which requires relatively great force for removal. The fastener has an annular locking ring provided within a groove in the head of the screw to allow the screw to sit within or flush with the anterior surface of the plate. The through-hole in the plate which receives the locking screw comprises an entrance, a collar section, an undercut, and an exit. The locking ring resides within the undercut. The locking ring has a leading surface that is chamfered or radiused and a trailing surface that is flat. The chamfer allows the locking ring to easily be inserted into the through-hole by interacting with a lead chamfer in the entrance. After installation, the flat trailing surface abuts a lip adjoining the collar section and the undercut and prevents the screw from being easily removed from the through-hole.

32 Claims, 16 Drawing Sheets

U.S. PATENT DOCUMENTS

| | | | |
|---|---|---|---|
| 1,572,770 A | 2/1926 | Colley | |
| 1,765,239 A | 6/1930 | Meurling | |
| 2,248,054 A | 7/1941 | Becker | |
| 2,376,089 A | 5/1945 | Savagean | |
| 2,401,856 A | 6/1946 | Brock | |
| 2,423,511 A | 7/1947 | Luben et al. | |
| 2,463,378 A * | 3/1949 | Hallerstrom | 411/81 |
| 2,489,870 A | 11/1949 | Dzus | |
| 2,494,229 A | 1/1950 | Collison | |
| 2,922,456 A | 1/1960 | Kann | |
| 3,023,925 A | 3/1962 | Sher | |
| 3,054,321 A | 9/1962 | Macchia | |
| 3,062,253 A | 11/1962 | Milheiser | |
| 3,138,188 A | 6/1964 | Tuozzo et al. | |
| 3,221,794 A | 12/1965 | Acres | |
| 3,414,154 A | 12/1968 | Rose et al. | |
| 3,426,364 A | 2/1969 | Lumb | |
| 3,465,803 A | 9/1969 | Ernest et al. | |
| 3,534,731 A | 10/1970 | Muller | |
| 3,560,132 A | 2/1971 | Gulistan | |
| 3,695,259 A | 10/1972 | Yost | |
| 3,741,205 A | 6/1973 | Markolf et al. | |
| 3,762,455 A | 10/1973 | Anderson, Jr. | |
| 3,770,036 A | 11/1973 | Sherman | |
| 3,774,244 A | 11/1973 | Walker | |
| 3,777,358 A | 12/1973 | Matievich et al. | |
| 3,894,467 A | 7/1975 | Brescia | |
| RE28,841 E | 6/1976 | Allgower et al. | |
| 4,001,928 A | 1/1977 | Scweiso | |
| 4,388,921 A | 6/1983 | Sitter et al. | |
| RE31,628 E | 7/1984 | Allgower et al. | |
| 4,484,570 A | 11/1984 | Sutter et al. | |
| 4,488,543 A | 12/1984 | Tornier | |
| 4,493,317 A | 1/1985 | Klaue | |
| 4,503,848 A | 3/1985 | Caspar et al. | |
| 4,512,038 A | 4/1985 | Alexander et al. | |
| 4,563,778 A | 1/1986 | Roche et al. | |
| 4,566,138 A | 1/1986 | Lewis et al. | |
| 4,599,086 A | 7/1986 | Doty | |
| 4,599,999 A | 7/1986 | Klaue | |
| 4,711,234 A | 12/1987 | Vives et al. | |
| 4,760,844 A | 8/1988 | Kyle | |
| 4,794,918 A | 1/1989 | Wolter | |
| 4,795,468 A | 1/1989 | Hodorek et al. | |
| 4,808,185 A | 2/1989 | Penenberg et al. | |
| 4,834,752 A | 5/1989 | Van Kampen | |
| 4,836,196 A | 6/1989 | Park et al. | |
| 4,892,545 A | 1/1990 | Day et al. | |
| 4,904,261 A | 2/1990 | Dove et al. | |
| 4,915,559 A | 4/1990 | Wheeler et al. | |
| 4,917,704 A | 4/1990 | Frey et al. | |
| 4,919,581 A | 4/1990 | Dubech | |
| 4,919,666 A | 4/1990 | Buchhorn et al. | |
| 4,955,325 A | 9/1990 | Zarnowski et al. | |
| 4,955,908 A | 9/1990 | Frey et al. | |
| 4,973,844 A | 11/1990 | O'Farrell et al. | |
| 5,021,062 A | 6/1991 | Adrey et al. | |
| 5,041,113 A | 8/1991 | Biedermann et al. | |
| 5,041,141 A | 8/1991 | Ypma et al. | |
| 5,049,150 A | 9/1991 | Cozad | |
| 5,053,034 A | 10/1991 | Olerud | |
| 5,053,036 A | 10/1991 | Perren et al. | |
| 5,057,111 A | 10/1991 | Park | |
| 5,059,075 A | 10/1991 | Kelly | |
| 5,073,070 A | 12/1991 | Chang | |
| 5,092,893 A | 3/1992 | Smith | |
| 5,123,926 A | 6/1992 | Pisharodi | |
| 5,129,899 A | 7/1992 | Small et al. | |
| 5,147,361 A | 9/1992 | Ojima et al. | |
| 5,147,367 A | 9/1992 | Ellis | |
| 5,151,103 A | 9/1992 | Tepic et al. | |
| 5,176,679 A | 1/1993 | Lin | |
| 5,180,388 A | 1/1993 | DiCarlo | |
| 5,209,751 A | 5/1993 | Farris et al. | |
| 5,234,431 A | 8/1993 | Keller | |
| 5,246,459 A | 9/1993 | Elias | |
| 5,261,910 A | 11/1993 | Warden et al. | |
| 5,263,987 A | 11/1993 | Shah | |
| 5,269,784 A | 12/1993 | Mast | |
| 5,282,864 A | 2/1994 | Noiles et al. | |
| 5,290,288 A | 3/1994 | Vignaud et al. | |
| 5,304,210 A | 4/1994 | Crook | |
| 5,312,404 A | 5/1994 | Asher et al. | |
| 5,320,626 A | 6/1994 | Schmieding | |
| 5,330,535 A | 7/1994 | Moser et al. | |
| 5,334,205 A | 8/1994 | Cain | |
| 5,338,197 A | 8/1994 | Kwan | |
| 5,344,421 A | 9/1994 | Crook | |
| 5,344,422 A | 9/1994 | Frigg | |
| 5,346,492 A | 9/1994 | Morgan | |
| 5,352,224 A | 10/1994 | Westermann | |
| 5,360,452 A | 11/1994 | Engelhardt et al. | |
| 5,364,399 A | 11/1994 | Lowery et al. | |
| 5,380,328 A | 1/1995 | Morgan | |
| 5,395,371 A | 3/1995 | Miller et al. | |
| 5,395,372 A | 3/1995 | Holt et al. | |
| 5,397,364 A | 3/1995 | Kozak et al. | |
| 5,398,664 A | 3/1995 | Betz | |
| 5,405,398 A | 4/1995 | Buford, III et al. | |
| 5,423,826 A | 6/1995 | Coates et al. | |
| 5,458,638 A | 10/1995 | Kuslich et al. | |
| 5,458,641 A | 10/1995 | Ramirez Jimenez | |
| 5,468,242 A | 11/1995 | Reisberg | |
| 5,470,333 A | 11/1995 | Ray | |
| 5,474,551 A | 12/1995 | Finn et al. | |
| 5,474,553 A | 12/1995 | Baumgart | |
| 5,476,463 A | 12/1995 | Boachie-Adjei et al. | |
| 5,486,176 A | 1/1996 | Hildebrand et al. | |
| 5,487,744 A | 1/1996 | Howland | |
| 5,520,690 A | 5/1996 | Errico et al. | |
| 5,531,554 A | 7/1996 | Jeanson et al. | |
| 5,531,746 A | 7/1996 | Errico et al. | |
| 5,534,027 A | 7/1996 | Hodorek | |
| 5,534,032 A | 7/1996 | Hodorek | |
| 5,534,731 A | 7/1996 | Cheung | |
| 5,545,163 A | 8/1996 | Miller et al. | |
| 5,549,608 A | 8/1996 | Errico et al. | |
| 5,549,612 A | 8/1996 | Yapp et al. | |
| 5,549,683 A | 8/1996 | Bonutti | |
| 5,558,480 A | 9/1996 | Kazino et al. | |
| 5,569,247 A | 10/1996 | Morrison | |
| 5,571,198 A | 11/1996 | Drucker et al. | |
| 5,578,034 A | 11/1996 | Estes | |
| 5,582,612 A | 12/1996 | Lin | |
| 5,591,557 A | 1/1997 | Lawson et al. | |
| 5,601,553 A | 2/1997 | Trebing et al. | |
| 5,607,426 A | 3/1997 | Ralph et al. | |
| 5,613,967 A | 3/1997 | Engelhardt et al. | |
| 5,616,144 A | 4/1997 | Yapp et al. | |
| 5,618,145 A | 4/1997 | Kuo | |
| 5,634,926 A | 6/1997 | Jobe | |
| 5,639,113 A | 6/1997 | Goss et al. | |
| 5,643,265 A | 7/1997 | Errico et al. | |
| 5,645,606 A | 7/1997 | Oehy et al. | |
| 5,647,873 A | 7/1997 | Errico et al. | |
| 5,653,710 A | 8/1997 | Harle | |
| 5,658,288 A | 8/1997 | Kim | |
| 5,669,911 A | 9/1997 | Errico et al. | |
| 5,676,666 A | 10/1997 | Oxland et al. | |
| 5,681,311 A | 10/1997 | Foley et al. | |
| 5,690,630 A | 11/1997 | Errico et al. | |
| 5,709,686 A | 1/1998 | Talos et al. | |
| 5,720,751 A | 2/1998 | Jackson | |
| 5,725,580 A | 3/1998 | Cloutier et al. | |

| | | | | | | | |
|---|---|---|---|---|---|---|---|
| 5,725,588 | A | 3/1998 | Errico et al. | 6,309,393 | B1 | 10/2001 | Tepic et al. |
| 5,735,852 | A | 4/1998 | Amrein et al. | 6,315,779 | B1 | 11/2001 | Morrison et al. |
| 5,735,853 | A | 4/1998 | Olerud | 6,331,179 | B1 | 12/2001 | Freid et al. |
| 5,741,255 | A | 4/1998 | Krag et al. | 6,342,055 | B1 | 1/2002 | Eisermann et al. |
| 5,741,258 | A | 4/1998 | Klaue et al. | 6,361,537 | B1 | 3/2002 | Anderson |
| 5,743,907 | A | 4/1998 | Asher et al. | 6,379,357 | B1 | 4/2002 | Bernstein et al. |
| 5,743,914 | A | 4/1998 | Skiba | 6,383,186 | B1 | 5/2002 | Michelson |
| 5,755,721 | A | 5/1998 | Hearn | 6,398,783 | B1 | 6/2002 | Michelson |
| 5,782,929 | A | 7/1998 | Sederholm | 6,402,756 | B1 | 6/2002 | Ralph et al. |
| 5,797,912 | A | 8/1998 | Runciman et al. | 6,402,759 | B1 | 6/2002 | Strong et al. |
| 5,807,396 | A | 9/1998 | Raveh | 6,413,259 | B1 | 7/2002 | Lyons et al. |
| 5,810,823 | A | 9/1998 | Klaue et al. | 6,416,528 | B1 | 7/2002 | Michelson |
| 5,814,046 | A | 9/1998 | Hopf | 6,428,542 | B1 | 8/2002 | Michelson |
| 5,817,094 | A | 10/1998 | Errico et al. | 6,440,135 | B2 | 8/2002 | Orbay et al. |
| 5,824,088 | A | 10/1998 | Kirsch | 6,454,769 | B2 | 9/2002 | Wagner et al. |
| 5,876,402 | A | 3/1999 | Errico et al. | 6,454,771 | B1 | 9/2002 | Michelson |
| 5,879,351 | A | 3/1999 | Viart | 6,458,133 | B1 | 10/2002 | Lin |
| 5,879,389 | A | 3/1999 | Koshino | 6,524,315 | B1 | 2/2003 | Selvitelli et al. |
| 5,882,350 | A | 3/1999 | Ralph et al. | 6,527,776 | B1 | 3/2003 | Michelson |
| 5,888,204 | A | 3/1999 | Ralph et al. | 6,533,786 | B1 | 3/2003 | Needham et al. |
| 5,888,205 | A | 3/1999 | Pratt et al. | 6,575,975 | B2 | 6/2003 | Brace et al. |
| 5,899,902 | A | 5/1999 | Brown et al. | 6,589,245 | B1 | 7/2003 | Weiler et al. |
| 5,902,303 | A | 5/1999 | Eckhof et al. | 6,592,586 | B1 | 7/2003 | Michelson |
| 5,904,683 | A | 5/1999 | Pohndorf et al. | 6,599,290 | B2 | 7/2003 | Bailey et al. |
| 5,911,758 | A | 6/1999 | Oehy et al. | 6,602,255 | B1 | 8/2003 | Campbell et al. |
| 5,913,860 | A | 6/1999 | Scholl | 6,602,256 | B1 | 8/2003 | Hayes |
| 5,931,838 | A | 8/1999 | Vito | 6,602,257 | B1 | 8/2003 | Thramann |
| 5,935,174 | A | 8/1999 | Dye | 6,605,090 | B1 | 8/2003 | Trieu et al. |
| 5,951,558 | A | 9/1999 | Fiz | 6,616,666 | B1 | 9/2003 | Michelson |
| 5,954,722 | A | 9/1999 | Bono | 6,620,163 | B1 | 9/2003 | Michelson |
| 5,961,554 | A | 10/1999 | Janson et al. | 6,623,486 | B1 | 9/2003 | Weaver et al. |
| 5,964,762 | A | 10/1999 | Biedermann et al. | 6,626,907 | B2 | 9/2003 | Blain et al. |
| 5,964,768 | A | 10/1999 | Huebner | 6,641,583 | B2 | 11/2003 | Shluzas et al. |
| 5,976,141 | A | 11/1999 | Haag et al. | 6,645,207 | B2 | 11/2003 | Dixon et al. |
| 5,993,451 | A | 11/1999 | Burkhart | 6,645,208 | B2 | 11/2003 | Apfelbaum et al. |
| 5,997,541 | A | 12/1999 | Schenk | 6,652,525 | B1 | 11/2003 | Assaker et al. |
| 6,017,345 | A | 1/2000 | Richelsoph | 6,669,700 | B1 | 12/2003 | Farris et al. |
| 6,030,162 | A | 2/2000 | Huebner | 6,679,883 | B2 | 1/2004 | Hawkes et al. |
| 6,030,389 | A | 2/2000 | Wagner et al. | 6,689,133 | B2 | 2/2004 | Morrison et al. |
| 6,036,697 | A | 3/2000 | DiCaprio | 6,695,846 | B2 | 2/2004 | Richelsoph et al. |
| 6,048,343 | A | 4/2000 | Mathis et al. | 6,712,818 | B1 | 3/2004 | Michelson |
| 6,059,785 | A | 5/2000 | Schavan et al. | 6,712,820 | B2 | 3/2004 | Orbay |
| 6,080,156 | A | 6/2000 | Asher et al. | 6,767,351 | B2 | 7/2004 | Orbay et al. |
| 6,090,111 | A | 7/2000 | Nichols | 6,793,656 | B1 | 9/2004 | Mathews |
| 6,113,601 | A | 9/2000 | Tatar | 6,863,671 | B1 | 3/2005 | Strobel et al. |
| 6,117,135 | A | 9/2000 | Schlapfer | 6,890,334 | B2 | 5/2005 | Brace et al. |
| 6,129,730 | A | 10/2000 | Bono et al. | 6,893,443 | B2 | 5/2005 | Frigg et al. |
| 6,129,770 | A | 10/2000 | Deutz et al. | 6,902,565 | B2 | 6/2005 | Berger et al. |
| 6,139,550 | A | 10/2000 | Michelson | 6,916,320 | B2 | 7/2005 | Michelson |
| 6,146,385 | A | 11/2000 | Torrie et al. | 6,926,718 | B1 | 8/2005 | Michelson |
| 6,152,927 | A | 11/2000 | Farris et al. | 6,936,050 | B2 | 8/2005 | Michelson |
| 6,159,213 | A | 12/2000 | Rogozinski | 6,936,051 | B2 | 8/2005 | Michelson |
| 6,193,721 | B1 | 2/2001 | Michelson | 6,945,972 | B2 | 9/2005 | Frigg et al. |
| 6,200,321 | B1 | 3/2001 | Orbay et al. | 6,945,973 | B2 | 9/2005 | Bray |
| 6,206,881 | B1 | 3/2001 | Frigg et al. | 6,945,974 | B2 | 9/2005 | Dalton |
| 6,206,882 | B1 | 3/2001 | Cohen | 6,945,975 | B2 | 9/2005 | Dalton |
| D440,311 | S | 4/2001 | Michelson | 6,964,664 | B2 | 11/2005 | Freid et al. |
| 6,214,005 | B1 | 4/2001 | Benzel et al. | 6,966,910 | B2 | 11/2005 | Ritland |
| 6,224,602 | B1 | 5/2001 | Hayes | 6,969,390 | B2 | 11/2005 | Michelson |
| 6,228,085 | B1 | 5/2001 | Theken et al. | 6,979,334 | B2 | 12/2005 | Dalton |
| 6,235,033 | B1 | 5/2001 | Brace et al. | 7,001,387 | B2 | 2/2006 | Farris |
| 6,235,034 | B1 | 5/2001 | Bray | 7,001,389 | B1 * | 2/2006 | Navarro et al. ................. 606/71 |
| 6,235,059 | B1 | 5/2001 | Benezech et al. | 7,048,739 | B2 | 5/2006 | Konieczynski |
| 6,241,731 | B1 | 6/2001 | Fiz | 7,070,599 | B2 | 7/2006 | Paul |
| 6,258,089 | B1 | 7/2001 | Campbell et al. | 7,074,221 | B2 | 7/2006 | Michelson |
| 6,261,291 | B1 | 7/2001 | Talaber et al. | 7,077,843 | B2 | 7/2006 | Thramann et al. |
| 6,261,293 | B1 | 7/2001 | Nicholson et al. | 7,077,844 | B2 | 7/2006 | Michelson |
| 6,273,889 | B1 | 8/2001 | Richelsoph | 7,094,237 | B2 | 8/2006 | Gradel |
| 6,280,445 | B1 | 8/2001 | Morrison et al. | 7,094,238 | B2 | 8/2006 | Morrison et al. |
| 6,290,703 | B1 | 9/2001 | Ganem | 7,094,242 | B2 | 8/2006 | Ralph et al. |
| D449,692 | S | 10/2001 | Michelson | 7,112,202 | B2 | 9/2006 | Michelson |
| 6,306,136 | B1 * | 10/2001 | Baccelli ...................... 606/279 | 7,112,223 | B2 | 9/2006 | Davis |
| 6,306,139 | B1 | 10/2001 | Fuentes | 7,137,984 | B2 | 11/2006 | Michelson |

| | | |
|---|---|---|
| 7,147,665 B1 | 12/2006 | Bryan et al. |
| 7,163,561 B2 | 1/2007 | Michelson |
| 7,169,150 B2 | 1/2007 | Shipp et al. |
| 7,172,627 B2 | 2/2007 | Fiere et al. |
| 7,175,625 B2 | 2/2007 | Culbert |
| 7,220,263 B2 | 5/2007 | Cordaro |
| 7,303,564 B2 | 12/2007 | Freid |
| 2001/0037112 A1 | 11/2001 | Brace et al. |
| 2002/0045898 A1 | 4/2002 | Freid et al. |
| 2002/0058939 A1 | 5/2002 | Wagner et al. |
| 2002/0120273 A1 | 8/2002 | Needham et al. |
| 2002/0128655 A1 | 9/2002 | Michelson |
| 2002/0151899 A1 | 10/2002 | Bailey et al. |
| 2002/0183754 A1 | 12/2002 | Michelson |
| 2003/0045878 A1 | 3/2003 | Petit et al. |
| 2003/0045880 A1 | 3/2003 | Michelson |
| 2003/0181912 A1 | 9/2003 | Michelson |
| 2003/0187440 A1 | 10/2003 | Richelsoph et al. |
| 2003/0199876 A1 | 10/2003 | Brace et al. |
| 2003/0208204 A1 | 11/2003 | Bailey et al. |
| 2003/0225409 A1 | 12/2003 | Freid et al. |
| 2004/0092930 A1 | 5/2004 | Petit et al. |
| 2004/0097935 A1 | 5/2004 | Richelsoph et al. |
| 2004/0158246 A1 | 8/2004 | Assaker et al. |
| 2004/0181226 A1 | 9/2004 | Michelson |
| 2004/0220570 A1 | 11/2004 | Frigg |
| 2004/0220572 A1 | 11/2004 | Michelson |
| 2004/0236334 A1 | 11/2004 | Michelson |
| 2004/0236335 A1 | 11/2004 | Michelson |
| 2005/0038436 A1 | 2/2005 | Michelson |
| 2005/0059971 A1 | 3/2005 | Michelson |
| 2005/0070899 A1 | 3/2005 | Doubler et al. |
| 2005/0187552 A1 | 8/2005 | Michelson |

FOREIGN PATENT DOCUMENTS

| | | |
|---|---|---|
| AU | 714659 | 1/2000 |
| CA | 2216955 | 10/1996 |
| CH | 674927 | 8/1990 |
| DE | 1046827 | 12/1958 |
| DE | 2933141 | 4/1980 |
| DE | 3442004 | 4/1986 |
| DE | 4409833 | 10/1995 |
| DE | 4409833 A1 | 10/1995 |
| EP | 0196206 | 10/1986 |
| EP | 0313762 | 10/1988 |
| EP | 0809974 | 4/1997 |
| EP | 0809975 | 5/1997 |
| EP | 1323390 | 7/2003 |
| EP | 1323390 A1 | 7/2003 |
| EP | 1393687 | 3/2004 |
| EP | 1393687 A2 | 3/2004 |
| EP | 1393688 | 3/2004 |
| EP | 1393689 | 3/2004 |
| EP | 1393689 A2 | 3/2004 |
| EP | 1402832 | 3/2004 |
| EP | 1402833 | 3/2004 |
| EP | 1402833 A2 | 3/2004 |
| EP | 1402834 | 3/2004 |
| EP | 1402835 | 3/2004 |
| EP | 1402835 A2 | 3/2004 |
| EP | 1402836 | 3/2004 |
| EP | 1402836 A2 | 3/2004 |
| FR | 2651996 | 9/1989 |
| WO | 8803781 | 6/1988 |
| WO | 8803781 A1 | 6/1988 |
| WO | 9103994 | 4/1991 |
| WO | 9426193 | 11/1994 |
| WO | 9426193 A1 | 11/1994 |
| WO | 9530389 | 11/1995 |
| WO | 9535067 | 12/1995 |
| WO | 9535067 A2 | 12/1995 |
| WO | 9603096 | 2/1996 |
| WO | 9608206 A1 | 3/1996 |
| WO | 9617564 | 6/1996 |
| WO | 9623457 | 8/1996 |
| WO | 9632071 | 10/1996 |
| WO | WO96/32071 | 10/1996 |
| WO | 9720513 | 6/1997 |
| WO | 9737620 | 10/1997 |
| WO | 9834553 A1 | 8/1998 |
| WO | 9834556 A1 | 8/1998 |
| WO | 02080819 | 10/2002 |
| WO | 02098276 | 12/2002 |
| WO | 02098277 | 12/2002 |
| WO | 03068092 | 8/2003 |
| WO | 03068092 A1 | 8/2003 |
| WO | 03068113 | 8/2003 |

OTHER PUBLICATIONS

R.W. Bailey et al., Stabilization of the Cervical Spine by Anterior Fusion, The Journal of Bone and Joint Surgery (American Volume), 1960, 565-594, vol. 42A, No. 4, University of Michigan, U.S.A.

R.C. Black et al., A Contoured Anterior Spinal Fixation Plate, Clinical Orthopaedics and Related Research, 1988, 135-142, vol. 227 (February) U.S.A.

J. Bohler, M.D., et al., Anterior Plate Stabilization for Fracture-dislocations of the Lower Cervical Spine, The Journal of Trauma, 1980, 203-205, vol. 20, No. 3, The William & Wilkins Co U.S.A.

D. Bynum, Jr., et al., Holding Characteristics of Fasteners in Bone, Experimental Mechanics, 1971, 363-369, August, Texas A & M University, U.S.A.

M. Cabanela, M.D., et al., Anterior Plate Stabilization for Bursting Teardrop Fractures of the Cervical Spine, Spine, 1988, 888-891, vol. 13, U.S.A.

S. Esses, The AO Spinal Internal Fixation, Spine, 1989, 373-378, vol. 14, Canada.

V. Goel, et al., Effects of Rigidity of an Internal Fixation Device, Spine, 1991, 155-161, vol. 16 Supp., U.S.A.

N. Haas, et al., Anterior Plating in Thorocolumbar Spine Injuries. Spine, 1991. 100-111, vol. 16 Supp., Germany.

D. Hall, et al., Anterior Plate Fixation in Spine Tumor Surgery, Spine, 1991, 80-83, vol. 16 Supp., United Kingdom.

E. Koranyi, et al., Holding Power of Orthopedic Screws in Bone, Clinical Orthopaedics and Related Research, 1970, 283-286, vol. 72 (Sep.-Oct.) U.S.A.

M. Krag, Biomechanics of Thorocolumbar Spinal Fixation, Spine, 1991, 84-99, vol. 16 Supp., U.S.A.

F. Lesoin, et al., The Anterior Approach and Plates in Lower Cervical Posttraumatic Lesions, Surg Neurol, 1984, 581-587, vol. 21, Elsevier Science Publishing Co., Inc., France.

M.E. Muller, et al., The Spine, Manual of Internal Fixation, 1991, 627-682, Germany.

J. Thalgott, M.D., et al., Reconstruction of the Lumbar Spine Using AO DCP Plate Internal Fixation, Spine, 1989, 91-95, vol. 14, U.S.A.

J. Zucherman, M.D., et al. Early Results of Spinal Fusion Using Variable Spine Plating System, Spine, 1988, 570-579, vol. 13, U.S.A.

Howard S. An and Jerome M. Cotler; Spinal Instrumentation; 1992; pp. 1-32; Williams & Wilkins; Baltimore, Maryland; USA.

* cited by examiner

FIXED AND VARIABLE LOCKING FIXATION ASSEMBLY

CROSS-REFERENCE TO RELATED APPLICATION

This application is a divisional application and claims priority to co-pending patent application Ser. No. 10/190,257, filed on Jul. 5, 2002.

BACKGROUND OF THE INVENTION

The present invention relates generally to locking fixation assemblies. More specifically, the present invention relates to a fixed and variable locking screw that can be used in bone fixation assemblies.

In the art of orthopedic fixation, it has become common for surgeons to utilize fixation plates for the treatment of spinal disorders including spinal anomalies, spinal injuries, disc problems, and bone problems. Indeed, within the past several years, the use of fixation plates for the treatment of spinal disorders or for fusion of vertebrae has grown considerably, and spinal plates have found increased use and desirability in the cervical spine as well.

As adequately described by Dr. Howard S. An and Dr. Jerome M. Cotler in the publication entitled *Spinal Instrumentation*, the upper cervical spine can be approached either anteriorly or posteriorly, depending upon the spinal disorder to be treated. This text discusses the fact that severe complications associated with procedures involving the upper cervical spine can be catastrophic, including injuries to the brain stem, spinal cord, or vertebral arteries, not to mention damage to the esophagus. These complications for upper cervical spine procedures are in addition to the normal complications associated with exposure and fusion of the cervical spine, implantation of a spinal fixation plate, and general disturbance of the spine.

In procedures involving the cervical spine, additional difficulties are encountered as a direct result of the small space in which the surgeon has to operate. When the upper cervical area is dissected, surgeons often find it difficult to maneuver because dissection is intimately close to vital neural, vascular, and visceral structures. As a result, surgeons have little room to operate, and even less room to manually position bone implant structures.

In the typical orthopedic fixation assembly, an orthopedic plate is attached to an adjacent bone by one or more fasteners, typically screws. As is well-known, any device implanted into the human body can cause some type of tissue reaction to the implanted foreign material. Also, in some instances, there are definite anatomic limits to the size of fastener which may be employed for a particular condition. One area where the anatomic limit is particularly notable is in the upper cervical region. For these reasons it is sometimes desirable to use the smallest feasible fasteners for fixating bone segments.

Successful use of spinal instrumentation in the anterior cervical spine is particularly difficult since limited space is available due to anatomic constraints. Any instrumentation implanted in the region must be minimally intrusive, yet have adequate strength to withstand the biomechanical loads to which it will be subjected. Current treatment methods also call for instrumentation which is able to provide both rigid fixation and semi-rigid or dynamized fixation that allows the implant to accommodate graft settling.

In anterior cervical applications in particular, orthopedic implants must be of very small size given the anatomical constraints related to work in this region. As a result, any implant to be placed in this region must be not only of diminutive length and width, but must also be of very small height in order to not protrude into the adjacent tissue or visceral structures. Ideally, it has been found that implants having a total thickness on the order of about 3.0 millimeters or less are acceptable. However, many prior art devices have total thicknesses in the range of 3 to 4 mm thick or more. Such thicknesses increase the risk of damage to the surrounding tissue, esophagus, and other vital anatomical structures.

An additional problem encountered with anterior cervical instrumentation is that, over time, the fixation screws tend to back out or loosen with respect to the remaining implant components. Such loosening, while sometimes benign, often leads to failure of the instrumentation systems. Screw loosening or screw migration can have catastrophic consequences in the case of cervical spine fixation, where a loose screw can penetrate the esophagus causing infection. Furthermore, it is important that bone screws are not installed using such a high torque as to strip the bone threads, especially when poor quality bone is encountered.

A number of systems employ various mechanical methods for preventing screw back out, nearly all of which employ some sort of secondary locking screw. Such a secondary locking screw increases the complexity and cost of the device, the surgical time required for implantation, and increases the chance for error on the part of the surgeon. Furthermore, other systems have attempted to employ a locking ring located in the shaft of the bone fixation screw. Such devices are inadequate in several respects. First, due to the anatomic constraints in the upper cervical region, screws employing a locking ring in their shaft necessarily are too long for proper use in cervical implantation. In order to have a sufficient length of threads and a sufficient length of shaft, the resulting screw is too long for safe use. Furthermore, screws employing a locking ring in the shaft usually employ a head section that must rest on top of the implant plate. Such arrangement is not desired, and indeed can be dangerous, as it results in an implant structure having a screwhead protruding above the plate. This protrusion can lead to infection as well as possible penetration of the surrounding tissue and anatomic structures.

As a result, the need exists for an implant system that provides a means of locking the bone fixation screw into the implant to prevent backout or screw migration. In addition, the need exists for such a system to be provided in implants suitable for small surgical areas, such as the upper cervical region. This necessarily requires a system that can be made of very small size, yet still have the desired locking properties. In addition, the need exists for such a system wherein the head of the screw is able to sit flush with or below the uppermost surface of the implant plate. Furthermore, the need exists for such a system that allows the surgeon to activate the locking mechanism using relatively minimal force, and in which the locking mechanism requires relatively great force to disengage.

BRIEF SUMMARY OF THE INVENTION

Accordingly, the present invention is directed to an implant system suitable for use in small regions such as the cervical spine region, that provides a locking screw having a locking ring located within the head of the screw. The locking ring comprises a lead chamfer or radius on the leading side of the ring that engages a mating lead-in chamfer in the fastener through-hole of the plate. The general term chamfer is defined herein as any rounding, angling, or beveling of a given surface or corner to facilitate a smoother transition from one area to another. The fastener of the present invention can be either of fixed (that is, rigid fixation) or variable (that is, semi-rigid or dynamized fixation) design, thus accommodating any type of fixation desired by the surgeon.

For the purposes of discussion and ease of understanding the system of the present invention will be described as applicable to a bone fixation plate system wherein an orthopedic plate is affixed to one or more bones located in the body. However it is to be understood that the present invention is applicable to other structures requiring a fastener that is easily screwed into the plate, yet requires relatively great force to remove it from the plate. In particular, this invention finds use in constructs wherein retaining the screw in the plate is important, and also where it is important that the head of the screw not protrude above the member into which it is screwed.

According to one embodiment of the present invention, there is provided a fastener comprising a head, a shank, and a threaded section wherein the head further comprises a recessed retaining ring therein. The retaining ring is of a split ring design, preferably having a generally circular shape. However, other shapes are contemplated, such as, without limitation, hexagonal, octagonal, n-tagonal, and so forth. In order to provide the desired easy entrance and difficult removal, the retaining ring comprises a leading edge chamfer or radius. This chamfer mates with an accompanying lead-in chamfer located within a portion of the fastener through-hole in the plate. These chamfers mate during insertion of the screw and provide a force vector which easily compresses (radially) the notched ring outside diameter allowing it to pass through the plate entry hole.

The preferred plate comprises fastener through-holes having several distinct sections. The uppermost section, the entrance, has a first diameter and a second diameter, wherein the first diameter is greater than the second diameter, and has sidewalls that are chamfered so that as a screw with a retaining ring is inserted through this portion of the hole, the chamfer gradually provides a compressive force that radially compresses the retaining ring. Once the retaining ring passes through the entrance of the hole, it enters a collar section of the hole, which comprises a cylindrical opening of constant diameter. The diameter of the collar section is less than the outer diameter of the retaining ring. Once the retaining ring passes through the collar section, it enters an undercut section of the hole. The undercut comprises an enlarged opening to allow the retaining ring to expand to nearly, but not completely, its original diameter. At the bottom of the undercut is a ramp portion of the hole which comprises a second chamfer or reduced diameter to allow angular movement of variable screws that may be utilized. When such screws are installed at an angle relative to the centroidal axis of the through-hole, the retaining ring would have the tendency to expand as the angle of entry increases. The chamfer provided in this section of the through-hole ensures that a positive compressive force is maintained in the radial direction on the retaining ring. The fifth, or exit, section of the through-hole contains a further reduced diameter section having a diameter just slightly greater than a diameter of a shoulder section at the base of the cylindrical portion of a fixed screw head so that the fixed screw fits snugly into the exit of the through-hole in order to prevent angular rotation of the screw while retained in the through hole. Alternatively, the variable screws have a shoulder diameter slightly smaller than the corresponding diameter of the fixed screws and a partial spherical section at the base of the head instead of the corresponding cylindrical section on the fixed screw, such that the variable screw may toggle while retained in the through-hole. To further facilitate such toggling, the top portion of the screw of the variable angle screw head has a chamfer or partial spherical section that rotates within the undercut section.

BRIEF DESCRIPTION OF THE DRAWINGS

The teachings of the present invention can be readily understood by considering the following detailed description of the preferred embodiment in conjunction with the accompanying drawings, in which.

DETAILED DESCRIPTION OF THE PREFERRED EMBODIMENT

While the present invention will be described more fully hereinafter with reference to the accompanying drawings, in which particular embodiments and methods are shown, it is to be understood from the outset that persons of ordinary skill in the art to may modify the invention herein described while achieving the functions and results of this invention. Accordingly, the descriptions which follow are to be understood as illustrative and exemplary of specific embodiments within the broad scope of the present invention and not as limiting the scope of the invention. Similarly, the present invention is applicable to any structure requiring a fastener, such as a screw 10, that is easily installed in a plate-like member, yet requires relatively great force to remove it from the plate-like member. For the purposes of discussion and ease of understanding, the system of the present invention will be described herein as applicable to a bone fixation plate system wherein an orthopedic plate 30 is affixed to one or more bones located in the body by means of one or more fasteners 10 through one or more through-holes 32. In particular, this invention finds use in constructs wherein it is important that the head of the screw not protrude above the member into which it is screwed. In the following descriptions, like numbers refer to similar features or like elements throughout.

Figure 1:
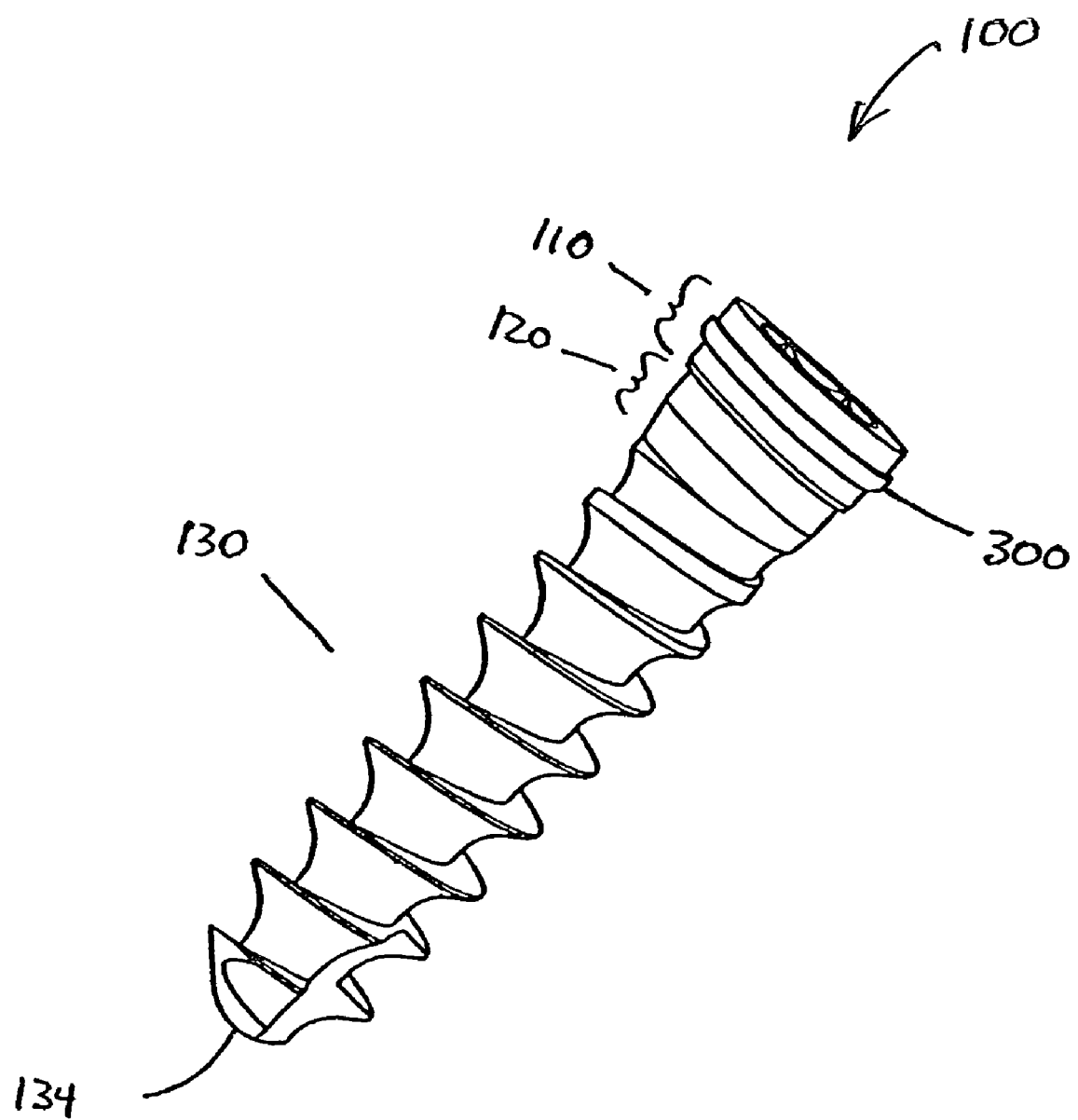
FIG. 1 is a perspective view of a fixed locking screw according to a preferred embodiment of the present invention.

FIG. 1 depicts, in general form, a locking screw according to a preferred embodiment. In particular, FIGS. 1-5 shows a fixed locking screw 100 as distinguished from FIGS. 6-10 which depict a variable locking screw 200 (to be described below, wherein the variable locking screw 200 has a modified head 210 and shank 220). The numeral 10 shall refer to a locking screw of the present invention without regard for whether it is of the fixed type or the variable type. Each of these types of screws will be described below.

Fixed Locking Screw 100

The fixed locking screw 100 generally comprises a head 110, a shank 120, and a threaded section 130. Each of these sections has a proximal end and a distal end, the proximal end being defined as that end closest the head 110 of the locking screw 100. The locking screw 100 may be made of various materials, including metallic and non-metallic, depending on the application involved and the stresses expected in vivo. In the preferred embodiment relating to cervical implant systems, the screw 100 is made of implant grade titanium (Ti-6Al-4V) per ASTM F-136.

The threaded section 130 can comprise various forms of threads 131, including but not limited to cancellous, cortical, and machine screw threads. In addition, the threads 131 may be self-tapping or non-self-tapping. Typically, the threaded section 130 comprises a major diameter 132, defined as the outer-most diameter of the threads 131, and a minor diameter 133 defined as the innermost or root diameter of the threads 131.

Figure 3:
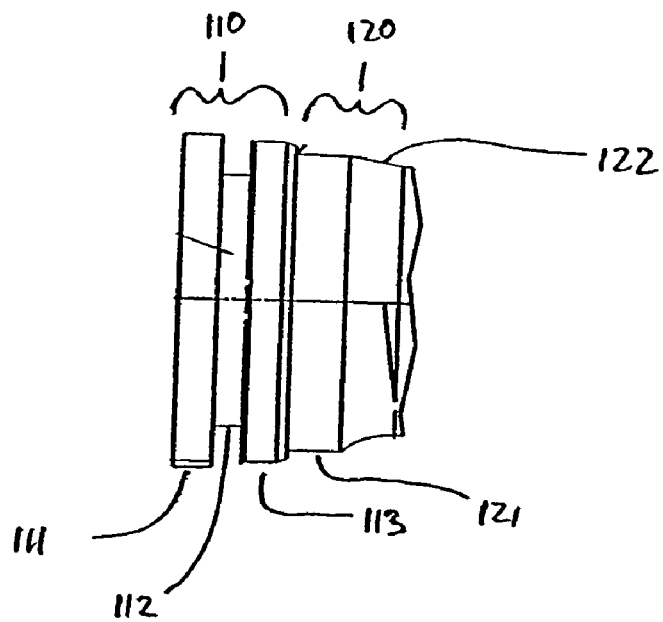
FIG. 3 is a detail view of the head of a fixed locking screw according to a preferred embodiment of the present invention.

FIG. 3 shows a close-up view of the head 110 and shank 120. The shank 120 is located between the threaded section 130 and the head 110. The shank 120 preferably comprises a first region, termed a shoulder 121, and a second region, termed a shoulder taper 122. The shoulder taper 122 is adjacent the proximal end of the threaded section 130.

The head 110 preferably further comprises three regions: an upper region 111, a groove 112, and a lower region 113. In the preferred fixed screw embodiment, depicted in FIGS. 1-5, the upper region 111 is a cylindrical section having a diameter and a height. Therefore, when viewed in cross-section the upper region 111 has parallel sidewalls. However, it should be appreciated that it may be possible for the upper region 111 to be conical, spherical, or of some other shape such that the upper region 111 has a first diameter at the proximal end and a second diameter adjacent the groove 112. In such embodiments, it is conceivable that the first diameter can be greater than the second diameter, or vice versa. In the preferred embodiment where the upper region 111 is a cylindrical section, however, it is obvious that the first diameter is equal to the second diameter, as the sidewalls are parallel in cross-section. It should be noted that the dimensions of the upper region 111 are dependent on the application, the materials used, and the stresses expected at that location. Therefore, the dimensions may vary significantly, from dimensions on the order of about a millimeter for anterior cervical applications, to theoretically any dimension for other, larger applications. In the preferred fixed screw embodiment, the upper region 111 has a height of approximately 0.58 mm (0.023 inches) and a diameter of approximately 4.79 mm (0.1886 inches).

At the distal end of the upper region 111 is the proximal end of the groove 112. The groove 112 is a section of reduced diameter that receives a locking ring 300. As with the upper region 111, the groove 112 has a diameter and a height. The diameter of the groove 112 is less than the internal diameter of the locking ring 300 (described below). In the preferred embodiment, the diameter of the groove 112 is approximately 3.69 mm (0.145 inches). Likewise, in the preferred embodiment, the height of the groove 112 is approximately 0.51 mm (0.020 inches). However, as with the dimensions of the upper region 111, the dimensions of the groove 112 are similarly variable.

The head 110 further comprises a lower region 113 having a proximal end and a distal end. The proximal end of the lower region 113 is adjacent the distal end of the groove 112. In the preferred embodiment, the proximal end of the lower region 113 is a cylindrical section having a diameter and a height. Therefore, when viewed in cross-section, the lower region 113 has parallel sidewalls. As with the upper region 111, however, the lower region 113 may also take on a non-cylindrical shape in alternative embodiments. In such embodiments, the lower region 113 may have a first diameter adjacent the groove 112 and a second diameter adjacent the shank 120, wherein the first and second diameters are not equal. However, as stated, in the preferred embodiment, the first and second diameters of the lower region 113 are equal. The distal end of the lower region 113 has a chamfer having a diameter, wherein the chamfer acts as a guide when the screw is inserted. In the preferred embodiment, the diameter of the lower section 113 is approximately 4.67 mm (0.184 inches). Likewise, in the preferred embodiment, the height of the lower region 113 is approximately 0.64 mm (0.025 inches). However, as with the dimensions of the upper region 111, the dimensions of the lower region 113 are similarly variable.

The shank 120 of the screw 100 likewise has a proximal end and a distal end. The proximal end of the shank 120 is adjacent the distal end of the lower region 113. The shank 120 comprises at its proximal end a shoulder 121 having a uniform diameter, and therefore parallel sidewalls when viewed in cross-section. The diameter of the shoulder 121 is preferably equal to the diameter of the chamfer of the lower region 113. The shank 120 comprises at its distal end a shoulder taper 122. The purpose of the shoulder taper 122 is to engage an exit section of a through-hole in a plate member (to be described below).

Figure 2:
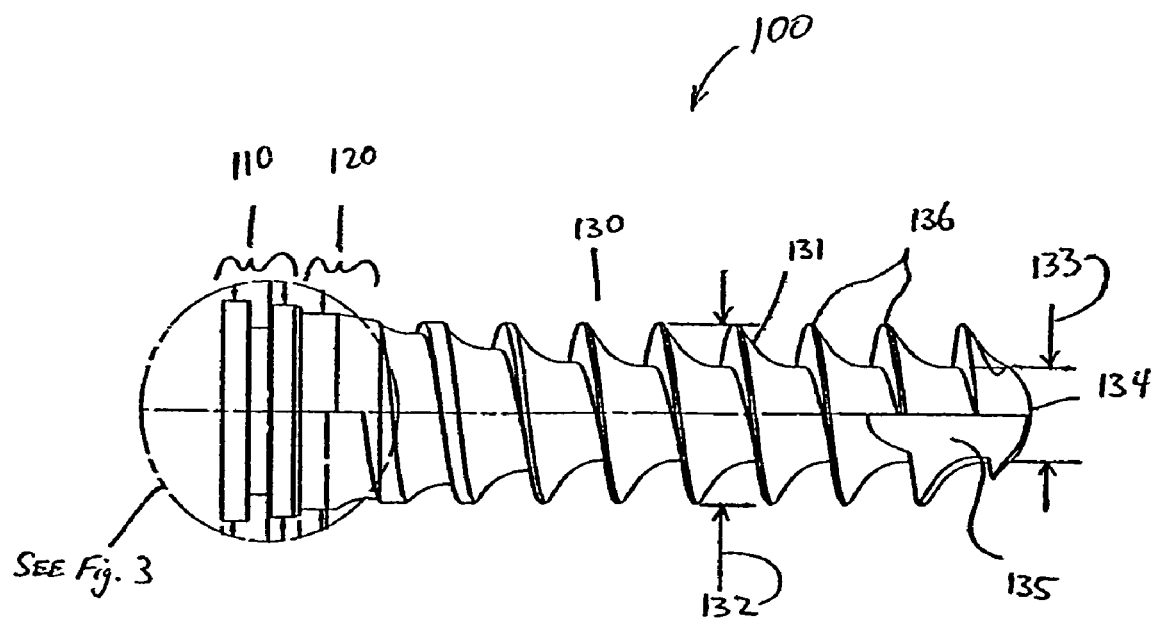
FIG. 2 is a plan view of a fixed locking screw according to a preferred embodiment of the present invention.

As best shown in FIG. 2, the threaded section 130 comprises threads 131, and has a proximal end and a distal end. The distal end of the threaded section 130 is the tip 134 of the screw 100. The proximal end of the threaded section 130 is adjacent the distal end of the shoulder taper 122 of the shank 120. The threads 131 may take many shapes and forms, depending in part on the type of application to which the screw is to be applied. In the preferred embodiment applicable to anterior cervical bone implant use, the threads 131 may be any type of cancellous bone thread, and can have a self-tapping region 135 if desired. In addition, the threaded section 130 has a major diameter 132 and a minor diameter 133. The major diameter 132 is the maximum outside diameter of a line tangent to each flute 136 of the threaded section 130. The minor diameter 133 or root diameter, is the minimum diameter of the threads 131, and can be understood to correspond with an imaginary shank portion extending throughout the length of the threaded section 130. In the preferred embodiment, the major diameter 132 is no greater than the diameter of the shoulder 121 of the shank 120. This is to facilitate installing the locking ring 300 (to be described below).

Figure 4:
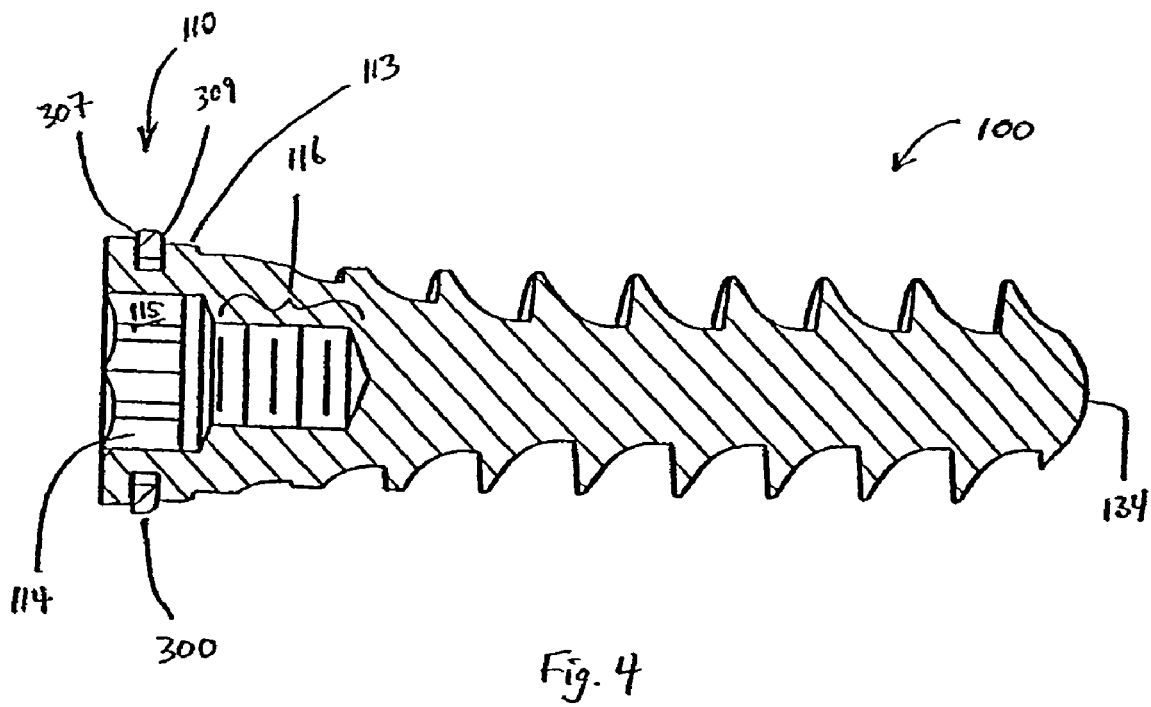
FIG. 4 is a cross-sectional view of the fixed locking screw of FIG. 1 according to a preferred embodiment of the present invention.
Figure 5:
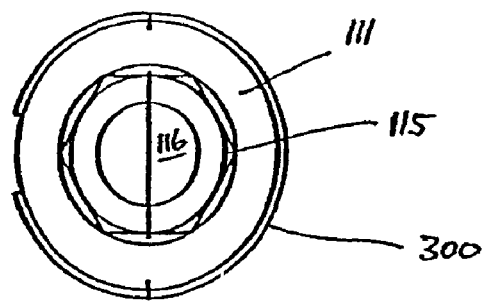
FIG. 5 is a top view of a fixed locking screw according to a preferred embodiment of the present invention.
Figure 6:
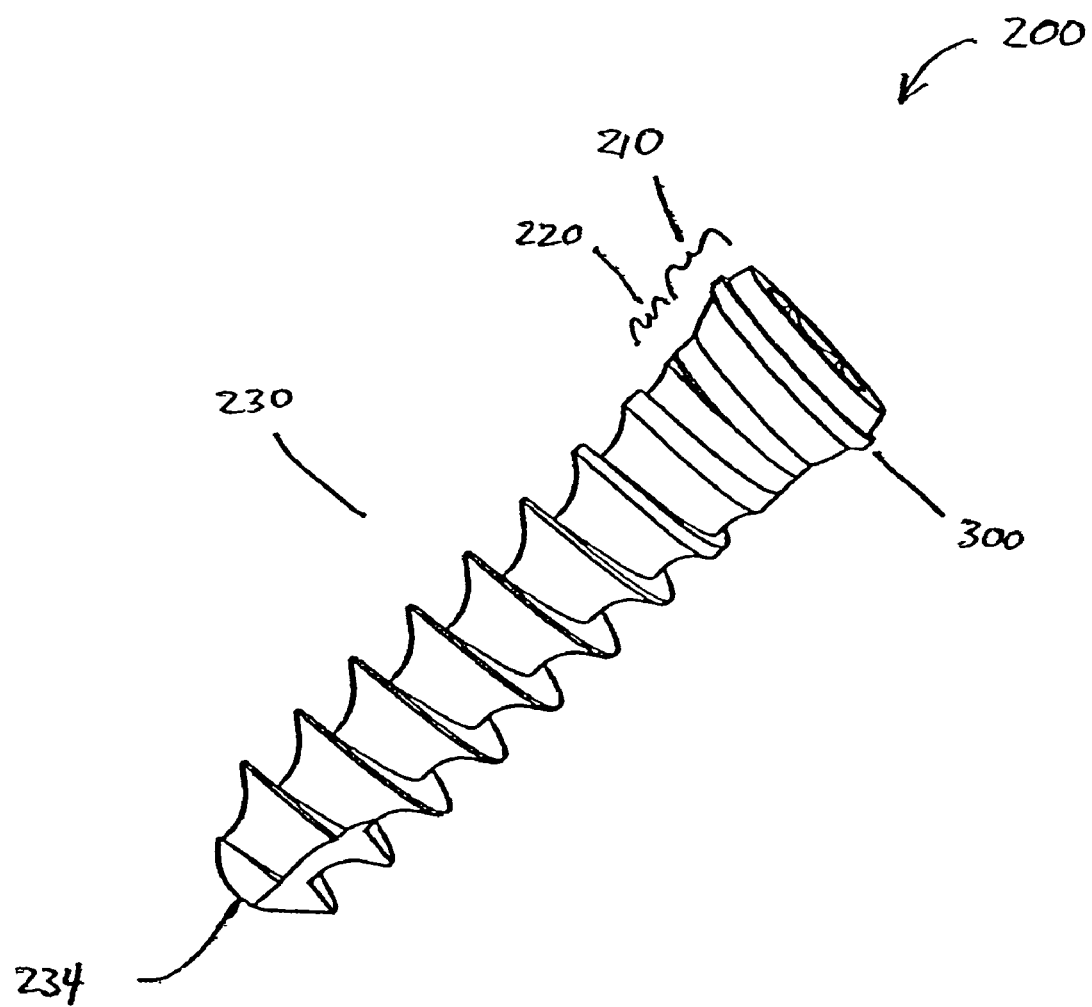
FIG. 6 is a perspective view of a variable locking screw according to a preferred embodiment of the present invention.
Figure 7:
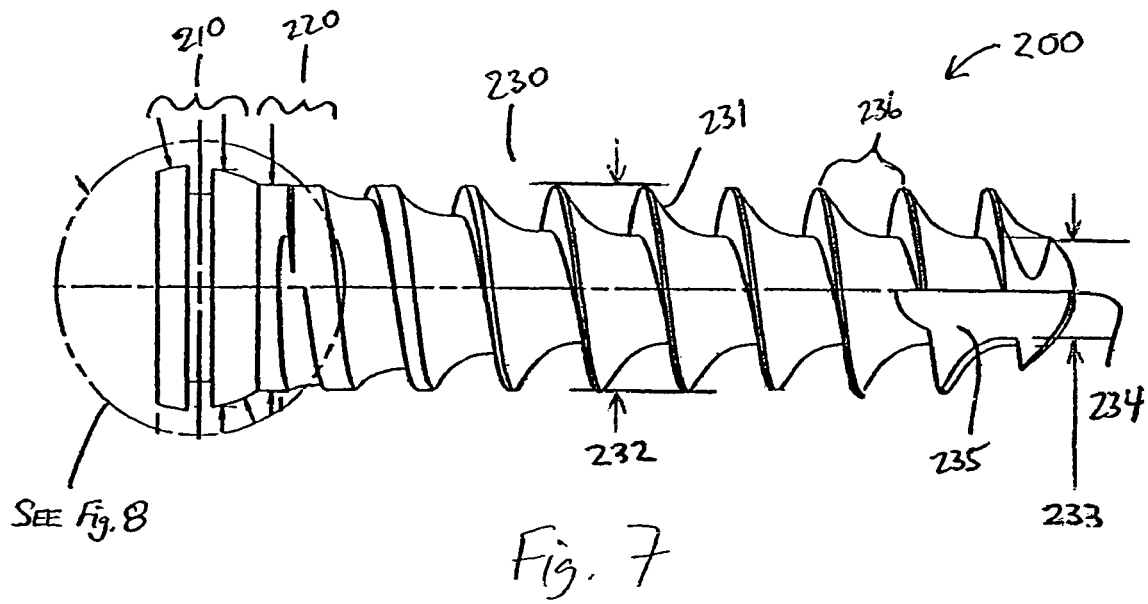
FIG. 7 is a plan view of a variable locking screw according to a preferred embodiment of the present invention.
Figure 8:
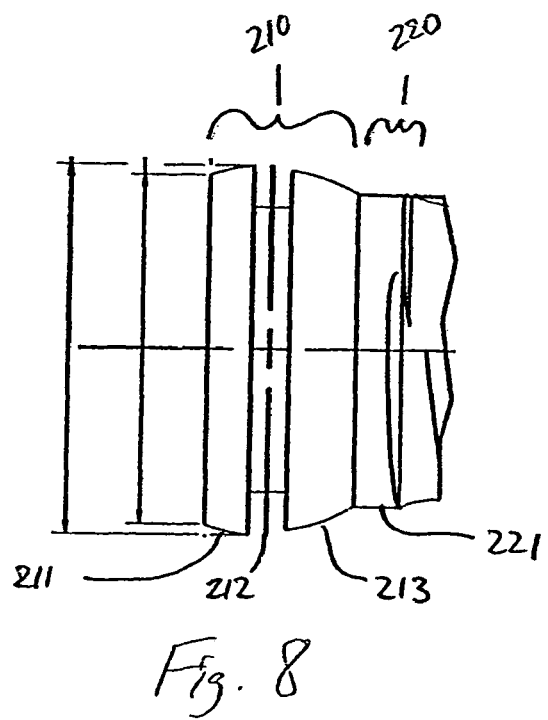
FIG. 8 is a detail view of the head of a variable locking screw according to a preferred embodiment of the present invention.
Figure 9:
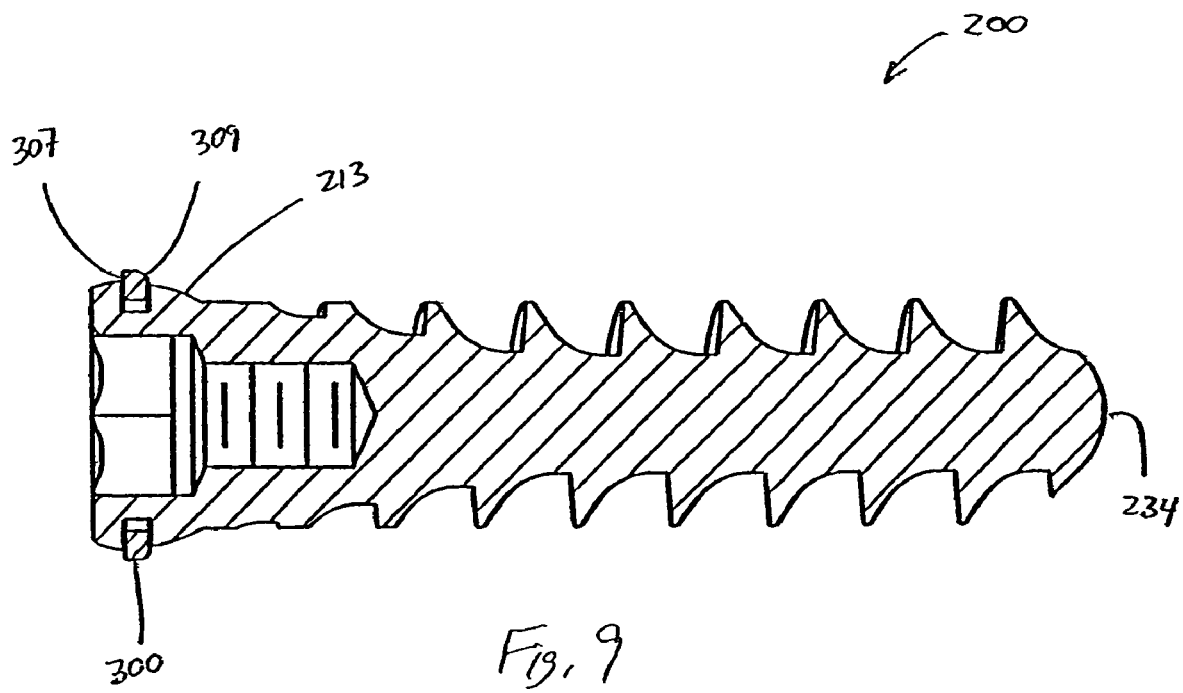
FIG. 9 is a cross-sectional view of a variable locking screw according to a preferred embodiment of the present invention.
Figure 10:
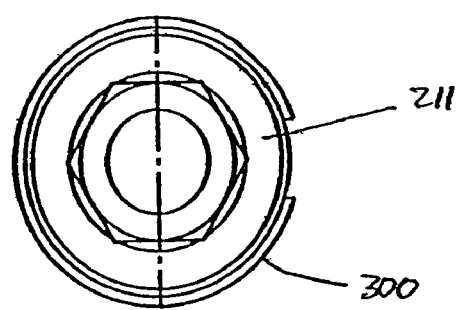
FIG. 10 is a top view of a variable locking screw according to a preferred embodiment of the present invention.
Figure 22:
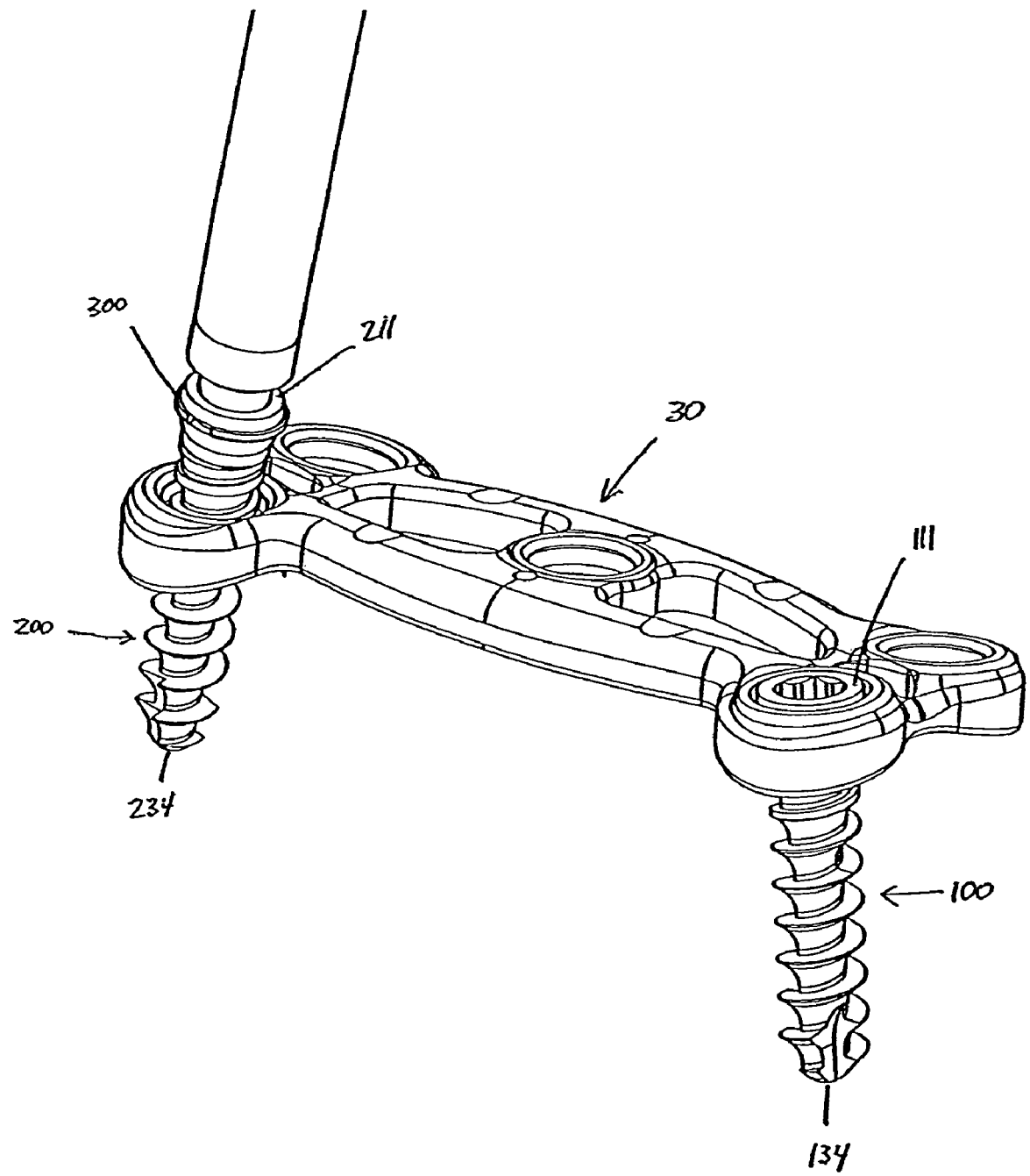
FIG. 22 is a perspective view of a plate having inserted therein a fixed locking screw and depicting a variable locking screw being inserted therein, according to a preferred embodiment of the present invention.

As best shown in FIGS. 4 and 5, preferably, the head 110 of the screw 100 further comprises an internal cavity 114 that receives the driving end of a driving instrument. In particular, the internal cavity 114 preferably comprises two sections: a first cavity section 115 and a second cavity section 116. The first cavity section 115 has an open entrance section and an open exit section, and comprises a female geometric cavity. This geometric cavity may take many shapes and sizes, including, but not limited to, slotted, cylindrical, tapered cylindrical, and any regular or irregular open polygonal shape. In the preferred embodiment, the first cavity section 115 comprises an internal hexagonal female opening that can receive a hex-headed male driving instrument. The second cavity section 116 is adjacent the exit section of the first cavity section 115 and preferably comprises an internal threaded section to receive male threads of a driving instrument. It should be noted that the second cavity section 116 need not comprise internal threads, but could comprise any open geometric shape that can releasably receive a driving instrument. The male threads of the driving instrument can be used to engage the female threads in the second cavity section 116, thereby drawing the screw 10 tight to the driving instrument. This is best seen in FIG. 22. In addition, the female threads in the second cavity section 116 can be used with a screw extraction device for removing a fastener 10 from the plate 30.

Locking Ring 300

Figure 11:
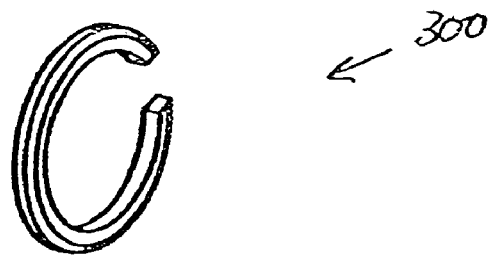
FIG. 11 is a perspective view of a locking ring according to a preferred embodiment of the present invention.
Figure 12:
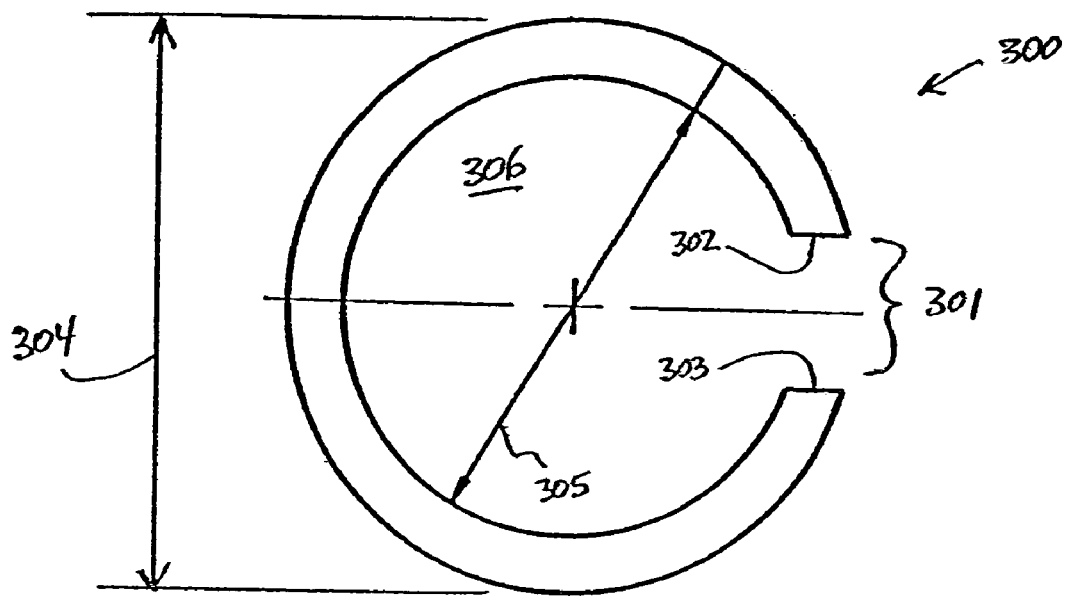
FIG. 12 is a plan view of the locking ring of FIG. 11 according to a preferred embodiment of the present invention.
Figure 13:
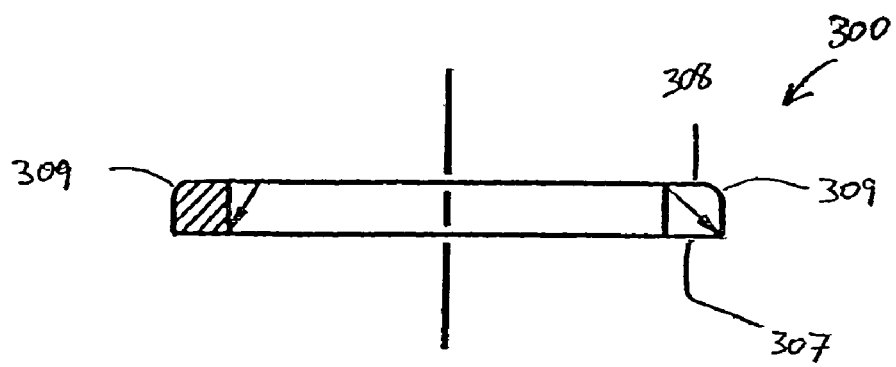
FIG. 13 is a cross-sectional view of the locking ring of FIG. 11 according to a preferred embodiment of the present invention.

As shown in FIGS. 11, 12, and 13, the locking ring 300 comprises a generally annular ring having a break 301 in its circumference, wherein the break 301 defines two opposing ring faces 302, 303. The locking ring 300 may take shapes that are not generally circular, but an annular ring is preferred. In any event, and for any of the contemplated shapes of the locking ring 300, the locking ring 300 generally has an outer diameter 304 and an inner diameter 305 which are preferably concentric about an imaginary centroidal axis. The inner diameter 305 thereby defines an opening 306 through which a screw 10 may be inserted in similar fashion to a standard washer. The locking ring 300 further comprises a trailing surface 307 and a leading surface 308. The trailing surface 307 is flat and is the opening through which the tip 134 of the screw 10 is first inserted. The leading surface 308, however, has a radius or chamfer 309 about its outer diameter 304. The locking ring 300 is designed to be inserted into the groove 112 in the head 110 of the screw 100. As stated previously, the inner diameter 305 of the locking ring 300 is greater than the diameter of the groove 112 of the head 110, but is less than the diameter of the cylindrical section of the lower region 113 of the head 110, and additionally is less than the maximum diameter of the upper region 111 of the head 110. Additionally, the outer diameter 304 of the locking ring 300 is greater than both the diameter of the upper region 111 of the head 110 and the diameter of the cylindrical section of the lower region 113 of the head 110. This ensures that, when the locking ring 300 is installed in the screw head 110, the locking ring 300 resides within the groove 112 of the head 110. The locking ring may be made from many materials, including metallic and non-metallic. In the preferred embodiment relating to cervical implant applications, the preferred material for the locking ring is an implant grade titanium (Ti-6A1-4V) per ASTM F-136.

It has been found that the diameter of both the shoulder 121 and the head 110 affect the amount the screw 100 is able to toggle within the through-hole 32. In addition, the locking ring 300 also plays a role in controlling the variability of the screw 100. If the force from screw toggling is transmitted through the locking ring 300 to the upper region 111 of the head 110 instead of the shank 120 of the screw 100, the locking ring 300 acting on the upper region 111 can cause the upper region 111 to fail after many cycles. As a result, a balance is preferable between the tolerance for mis-angled entry of the screw 100 and the risk for fatigue failure of the upper region 111 of the head 110. A preferable balance is achieved when the shoulder 121 diameter is 4.32 mm (0.170 inches) and the diameter of the head 110 is 4.85 mm (0.191 inches).

Figure 20:
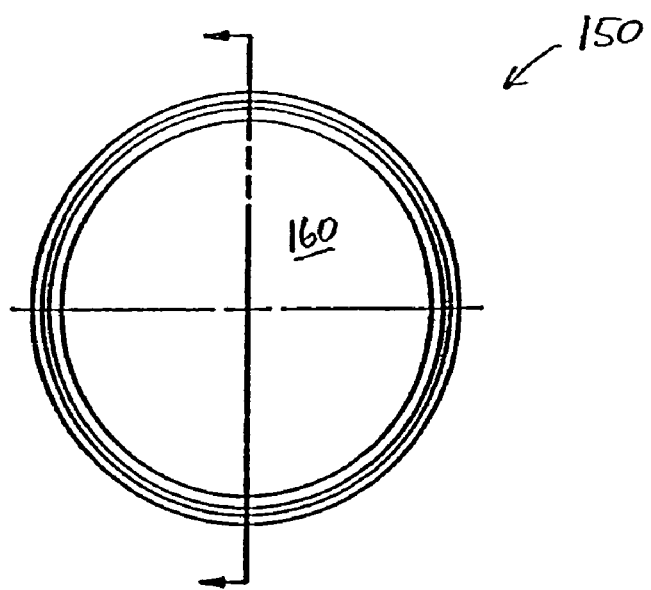
FIG. 20 is a top plan view of a sleeve for installing a locking ring on a fixed screw, according to a preferred embodiment.
Figure 21:
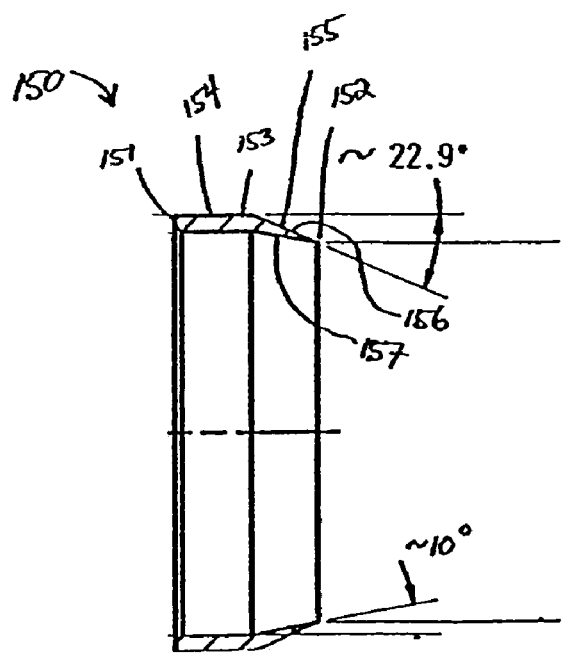
FIG. 21 is a section view of the sleeve of FIG. 20.

Installation of the locking ring 300 in the head 110 of the fixed locking screw 100 utilizes a sleeve 150, as shown in FIGS. 20 and 21. The sleeve 150 has a proximal end 151, a distal end 152, and a middle portion 153. The sleeve 150 is basically an annular cylindrical member defining an opening 160 therethrough. The proximal end 151 of the sleeve 150 has a straight sidewall portion 154 extending from the proximal end 151 to the middle portion 153, wherein the straight sidewall portion 154 has an outer diameter and an inner diameter. The outer diameter of the straight sidewall portion 154 is preferably equal to the diameter of the cylindrical section of the lower region 113 of the head 110. In the preferred embodiment, the outer diameter of the straight sidewall portion 154 is approximately 4.67 mm (0.184 inches). The inner diameter of the straight sidewall portion 154 is preferably equal to the diameter of the shoulder 121. In the preferred embodiment, the inner diameter is approximately 4.32 mm (0.170 inches).

The straight sidewall portion 154 is connected to a tapered sidewall portion 155 at the middle portion 153. The tapered sidewall portion 155 has an outer surface 156 and an inner surface 157. The inner surface 157 is tapered at the same angle as that of the shoulder taper 122 of the fastener 100. In the preferred embodiment, this taper is approximately 10°. Thus, the inner surface 157 of the preferred embodiment has a maximum diameter of approximately 4.32 mm (0.170 inches) and a minimum diameter at the distal end 152 of approximately 4.06 mm (0.160 inches). The outer surface 156 is also tapered, but is preferably tapered at a greater angle than is the inner surface 157. The purpose of the taper of the outer surface 156 is so provide a sort of ramp for the locking ring 300 to slide along, thus creating the radial force necessary to expand the locking ring 300 and allow it to be placed into the groove 112. In the preferred embodiment, the maximum diameter of the outer surface 156 is approximately 4.67 mm (0.184 inches) at the middle portion 153, and the minimum diameter is approximately 4.32 mm (0.170 inches) at the distal end 152.

To install the locking ring 300, the tip 134 of the screw 100 is first inserted through the opening 160 in the proximal end 151 of the sleeve 150. The sleeve 150 is then slid along the screw 100 until the proximal end 151 of the sleeve 150 rests against the distal end of the lower region 113 of the head 110 of the screw 100. Then, the tip 134 of the screw 100 is inserted through the opening 306 of the trailing surface 307 of the locking ring 300. The locking ring 300 is then moved along the length of the screw 100 toward the proximal end of the screw 100. Because the inner diameter 305 of the locking ring 300 is greater than the major diameter 132 of the threaded section 130, and is greater than the diameter of the shoulder 121 of the shank 120, the locking ring 300 easily is moved along the length of the screw 10. Once the locking ring 300 reaches the distal end 152 of the sleeve 150, the inner diameter 305 of the locking ring 300 begins to engage the outer surface 156 of the tapered sidewall portion 155 of the sleeve 150. As the locking ring 300 is moved farther along the screw 10 toward the proximal end of the screw 100, the locking ring 300 begins to expand in a radial direction as the outer surface 156 diameter becomes progressively larger than the inner diameter 305 of the locking ring 300. The radial expansion is allowed as a result of the break 301 in the circumference of the locking ring 300. This radial deformation is within the elastic region of the locking ring 300 so that no significant permanent deformation of the locking ring 300 occurs. Once the locking ring 300 surpasses the middle portion 153 of the sleeve 150, the inner diameter 305 of the locking ring 300 has then reached its maximum value, which is equal to the outer diameter of the straight sidewall portion 154 of the sleeve 150. Now the locking ring 300 is then able to be slid toward the groove 112 which, as described above, has a smaller diameter than the inner diameter 305 of the locking ring 300. As a result, the locking ring 300 then elastically springs back to its original shape and, because of the aforementioned respective diameters of the upper region 111, groove 112, and lower region 113, the locking ring 300 is retained within the groove 112 of the head 110. Now the locking screw assembly is complete and is ready for insertion into a plate 30.

Variable Locking Screw 200

Before describing the plate 30, the variable screw embodiment shall be described herein. Variable screws are desirable in many implant applications because of the differential graft settlement or movement that is likely to occur after implantation. In certain regions, such differential movement must be accounted for in some fashion to alleviate the resultant increased stresses on the fastening members that can be imposed by such movement. As a result, the variable screw 200 of the present invention is designed to accommodate such movement while eliminating or reducing the resultant stresses. Such movement is typically on the order of approximately 1 to 15° about the longitudinal axis of the through-hole 32.

FIGS. 6-10 depict the preferred embodiment of the variable locking screw 200. The variable locking screw 200 comprises, with several exceptions noted below, the same elements as the fixed locking screw 100 described above. In particular, the head 210 comprises an upper region 211, a groove 212, and a lower region 213. Furthermore, the shank 220 comprises a shoulder 221, and the threaded section 230 comprises threads 231 having a major diameter 232 and a minor diameter 233, the distal end of which is a tip 234.

However, it should be recognized from the Figures that some modifications exist in the head 210 and the shank 220 of the variable screw 200. In particular, the upper region 211 of the head 210 of the variable screw 200 comprises a generally spheroidal member having its outer sidewalls taking the shape of a portion of a sphere wherein the center of the sphere is located at a point along the longitudinal axis of the screw coincident with the center of the groove 212. More specifically, the proximal end of the upper region 211 has a first diameter and the distal end of the upper-region 211 has a second diameter, wherein the second diameter is greater than the first diameter and wherein the surface connecting the first diameter to the second diameter is a portion of a sphere the imaginary center of which is located at the intersection of the longitudinal axis of the screw 200 and a radial plane therethrough located at the midheight of the groove 212.

The groove 212 of the variable screw 200 is basically equivalent to the groove 112 of the fixed screw 100. However, as with the upper region 211 of the variable screw 200, the lower region 213 of the variable screw 200 comprises modifications from that of the fixed screw 100. In particular, the lower region 213 of the head 210 of the variable screw 200 comprises a generally spheroidal member having its outer sidewalls taking the shape of a portion of a sphere wherein the center of the sphere is located at a point along the longitudinal axis of the screw disposed slightly toward the proximal end of the screw 200 from the center of the groove 212. In the preferred embodiment, the imaginary center of this sphere is approximately 0.82 mm (0.032 inches) from the center of the groove 212. More specifically, the proximal end of the lower region 213 has a first diameter and the distal end of the upper region 213 has a second diameter, wherein the first diameter is greater than the second diameter and wherein the surface connecting the first diameter to the second diameter is a portion of a sphere the imaginary center of which is located at the intersection of the longitudinal axis of the screw 200 and a radial plane therethrough located at approximately 0.82 mm (0.032 inches) from the midheight of the groove 212.

Similarly, the shank 220 of the variable screw 200 is slightly different than the shank 120 of the fixed screw 100. In particular, the shoulder 221 of the variable screw 200 has a diameter that is very nearly equal to the major diameter 232 of the threads of the variable screw 200. As a result, there is no need for a shoulder taper on the variable screw 200. The shoulder 221 diameter is what controls the amount of toggle or variability allowed in the variable screw 200.

Because the variable screw 200 comprises a partially spherical lower region 213, there is no need to utilize the sleeve 150 in order to install the locking ring 300, as was the case for the fixed screw 100 (due to the fact that the lower region 113 of the fixed screw 100 comprises a cylindrical section). Rather, to install the locking ring 300 in the head 210 of the variable screw 200, the tip 234 of the screw 200 is first inserted through the opening 306 of the trailing surface 307 of the locking ring 300. The locking ring 300 is then moved along the length of the screw 200 toward the proximal end of the screw 200. Because the inner diameter 305 of the locking ring 300 is greater than the major diameter 232 of the threaded section 230, and is greater than the diameter of the shoulder 221 of the shank 220, the locking ring 300 easily is moved along the length of the screw 200. Once the locking ring 300 reaches the lower region 213 of the head 210, the inner diameter 305 of the locking ring 300 begins to engage the outer spherical surface of the lower region 213. As the locking ring 300 is moved farther along the screw 200 toward the proximal end of the screw 200, the locking ring 300 begins to expand in a radial direction as the spherical surface diameter becomes progressively larger than the inner diameter 305 of the locking ring 300. The radial expansion is allowed as a result of the break 301 in the circumference of the locking ring 300. This radial deformation is within the elastic region of the locking ring 300 so that no permanent deformation of the locking ring 300 occurs. Once the locking ring 300 surpasses the first diameter of the lower region 213 of the head 210, it reaches the groove 212 which, as described above, has a smaller diameter than the inner diameter 305 of the locking ring 300. As a result, the locking ring 300 then elastically springs back to its original shape and, because of the aforementioned respective diameters of the upper region 211, groove 212, and lower region 213, the locking ring 300 is retained within the groove 212 of the head 210. Now the locking screw assembly is complete and is ready for insertion into a plate 30.

Plate 30

Figure 14:
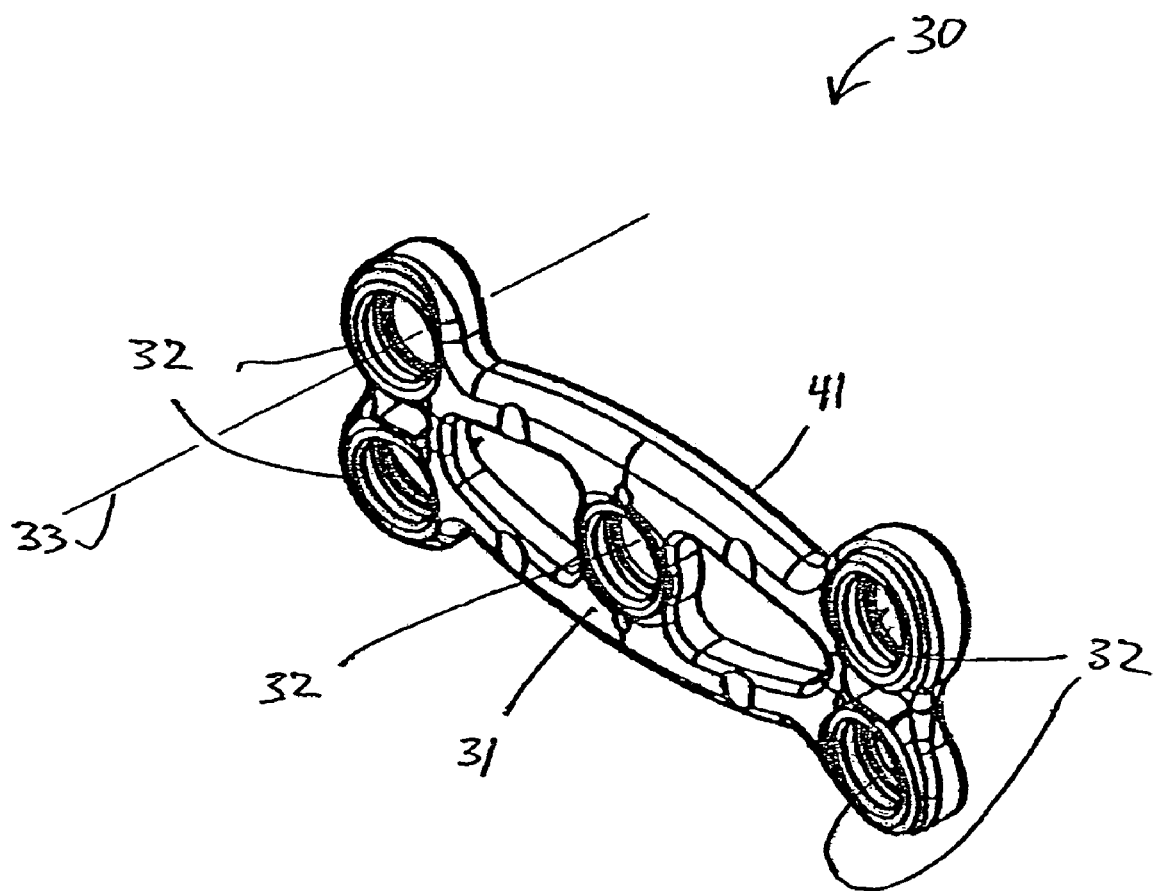
FIG. 14 is a perspective view of a plate according to a preferred embodiment of the present invention.
Figure 15:
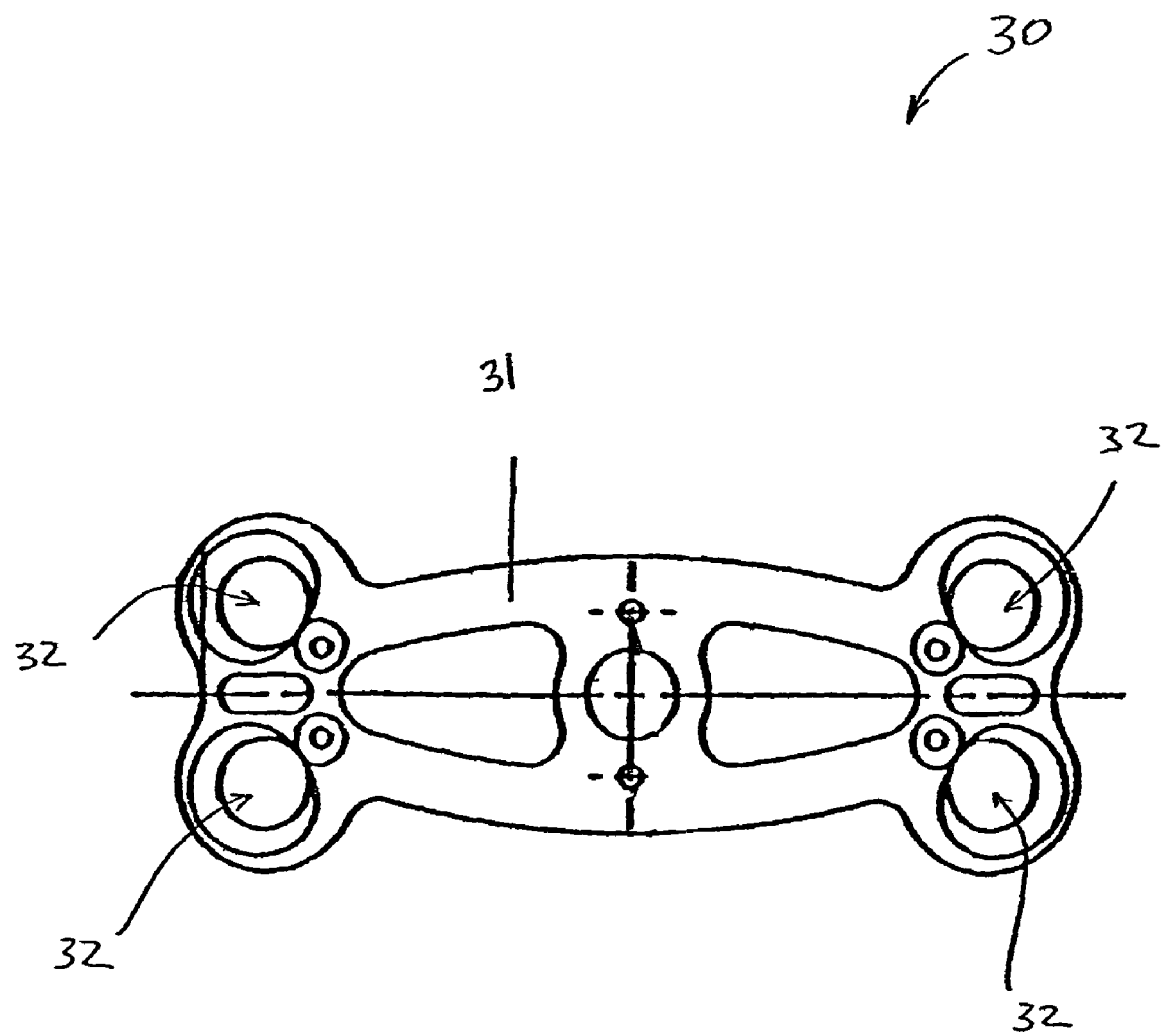
FIG. 15 is a bottom view of the plate of FIG. 14 according to a preferred embodiment of the present invention.
Figure 16:
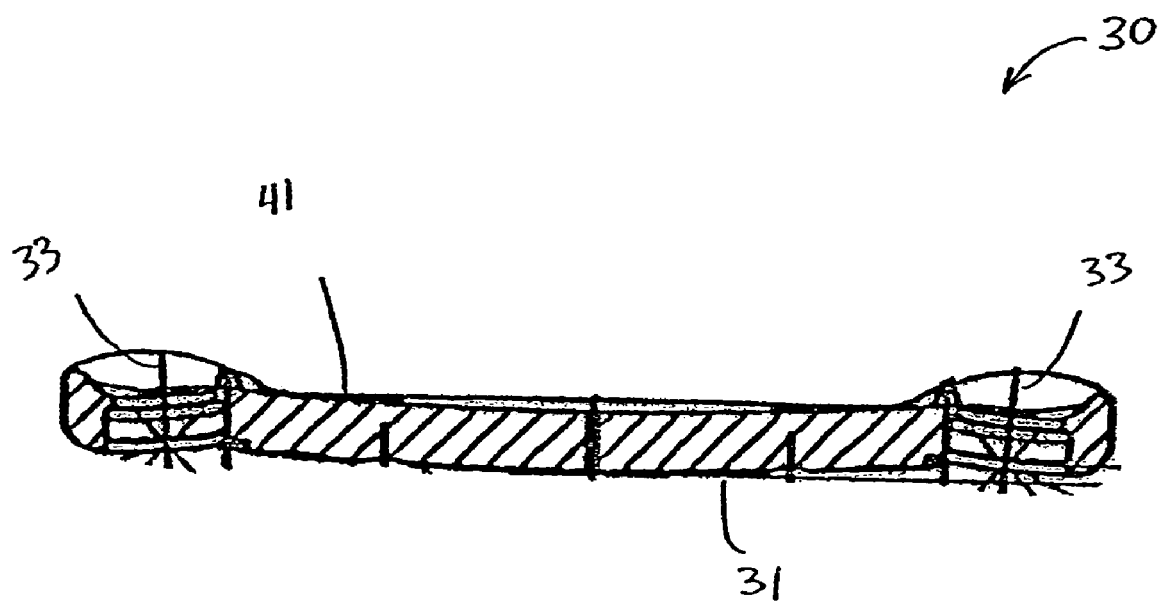
FIG. 16 is a cross-sectional view of a plate according to a preferred embodiment of the present invention.

Having described the fixed screw 100, the locking ring 300, and the variable screw 200 according to the preferred embodiments, it is now beneficial to describe the plate 30 of the preferred embodiment, shown generally in FIGS. 14-19. As stated, the plate 30 is a general term for the members into which the locking screws of the present invention are to be inserted. It is contemplated that the plate 30 may take various shapes, sizes, and forms, depending upon the type of use to be employed. In addition, it is contemplated that the plate 30 may be unrelated to medical implant devices. However, to more easily understand the present invention, the plate 30 will be described as a cervical fixation plate having an anterior (upper) surface 31 and a posterior (lower) surface 41 and a plurality of fastener through-holes 32 therein. The plate 30 shown in FIG. 14 is a two-level plate that spans two intervertebral disc levels. It should be understood that the plate 30 can also be a one level plate (spanning only one disc level) or any higher multiple level, the size of the plate 30 and the number of fastener through-holes 32 being adjusted accordingly. Each of the through-holes 32 comprises an imaginary longitudinal axis 33 perpendicular to the surface of the plate 30 through which the screws 10 will be inserted. FIGS. 14 through 16 depict a generalized cervical plate to facilitate this description. The portion of the plate 30 of interest herein is the through-hole 32.

Figure 17:
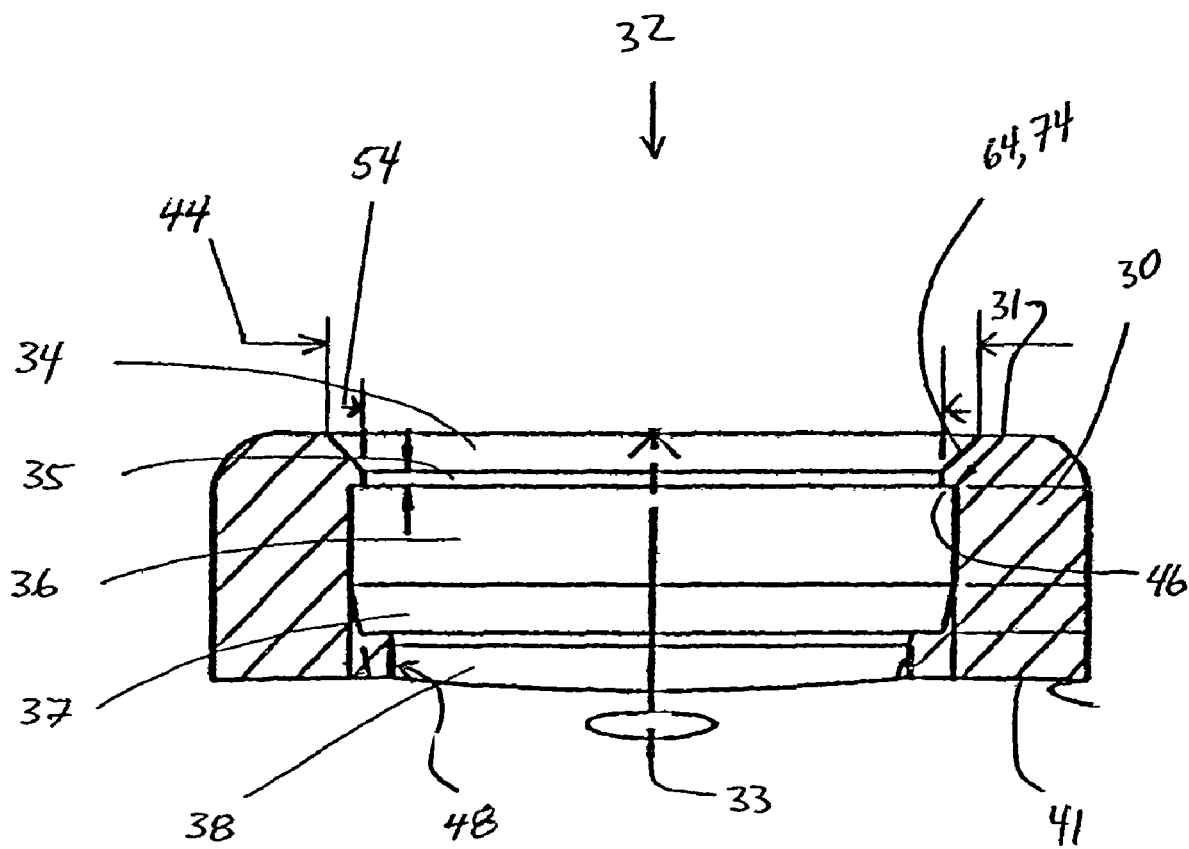
FIG. 17 is a detailed sectional view of a plate through-hole according to a preferred embodiment of the present invention.

FIG. 17 depicts a cross-section of a typical through-hole 32 according to the preferred embodiment. From this figure it can be seen that the through-hole 32 preferably comprises multiple sections. In the preferred embodiment, the through-hole 32 comprises an entrance 34 having a proximal end located at the anterior surface 31 of the plate 30. The entrance 34 further comprises a distal end located at a depth within the through-hole 32. The second section is a collar section 35 having its proximal end adjacent the distal end of the entrance 34. The third section is an undercut 36 having its proximal end adjacent the distal end of the collar section 35. The fourth section is a ramp section 37, and the fifth section is an exit 38. Throughout the following description, it should be remembered that each section of the through-hole 32 is adjacent the preceding section as one travels from the anterior surface 31 of the plate 30 toward posterior surface 41 of the plate 30. Each section has a proximal end and a distal end, the proximal end of each being defined as that end closest to the anterior surface 31 of the plate 30.

The entrance 34 has a first diameter 44 at or near its proximal end and a second diameter 54 at its distal end, wherein the first diameter 44 is greater than the second diameter 54. This creates a tapered sidewall 64. The tapered sidewall 64 serves the important function of providing the surface along which the leading surface 308 of the locking ring 300 contacts when the locking screw 100, 200 is inserted into the through-hole 32. The tapered sidewall 64 is a lead chamfer 74 that interacts with the leading surface 308 of the locking ring 300 (FIG. 13) so that as the locking ring 300 is progressed through the through-hole 32 in a direction away from the anterior surface 31, the lead chamfer 74 provides the necessary radial compressive force to begin radially compressing the locking ring 300, thereby elastically reducing the outer diameter 304 of the locking ring 300.

The collar section 35 comprises a cylindrical opening having parallel sidewalls. The diameter of the collar section 35 is greater than the inner diameter 305 of the locking ring 300, and represents the maximum extent to which the outer diameter 304 of the locking ring 300 is to be radially compressed.

The undercut 36 also comprises a cylindrical opening having parallel sidewalls, but the diameter of the cylindrical opening of the undercut 36 is greater than the diameter of the cylindrical opening of the collar section 35. By having a greater diameter than that of the collar section 35, there is created a lip 46 having, preferably, a 90° angle with respect to the parallel sidewalls of the undercut 36. This lip 46 provides a surface against which the trailing surface 307 of the locking ring 300 will bear when forces are applied on the screw 10 that would tend to remove the screw 10 from the through-hole 32. In addition, the diameter of the undercut 36 is slightly less than the outer diameter 304 of the locking ring 300 in its normal, uncompressed state. The purpose for this is so that when the locking ring 300 resides within the undercut 36, a certain level of radial compression resides in the locking ring 300. Stated otherwise, the locking ring 300 is not allowed to expand to its original and non-compressed state while it is present within the undercut 36. This reduces the amount of "play" in the screw/plate combination, and therefore provides a more desirable construct than is presently known in the prior art.

Figure 18:
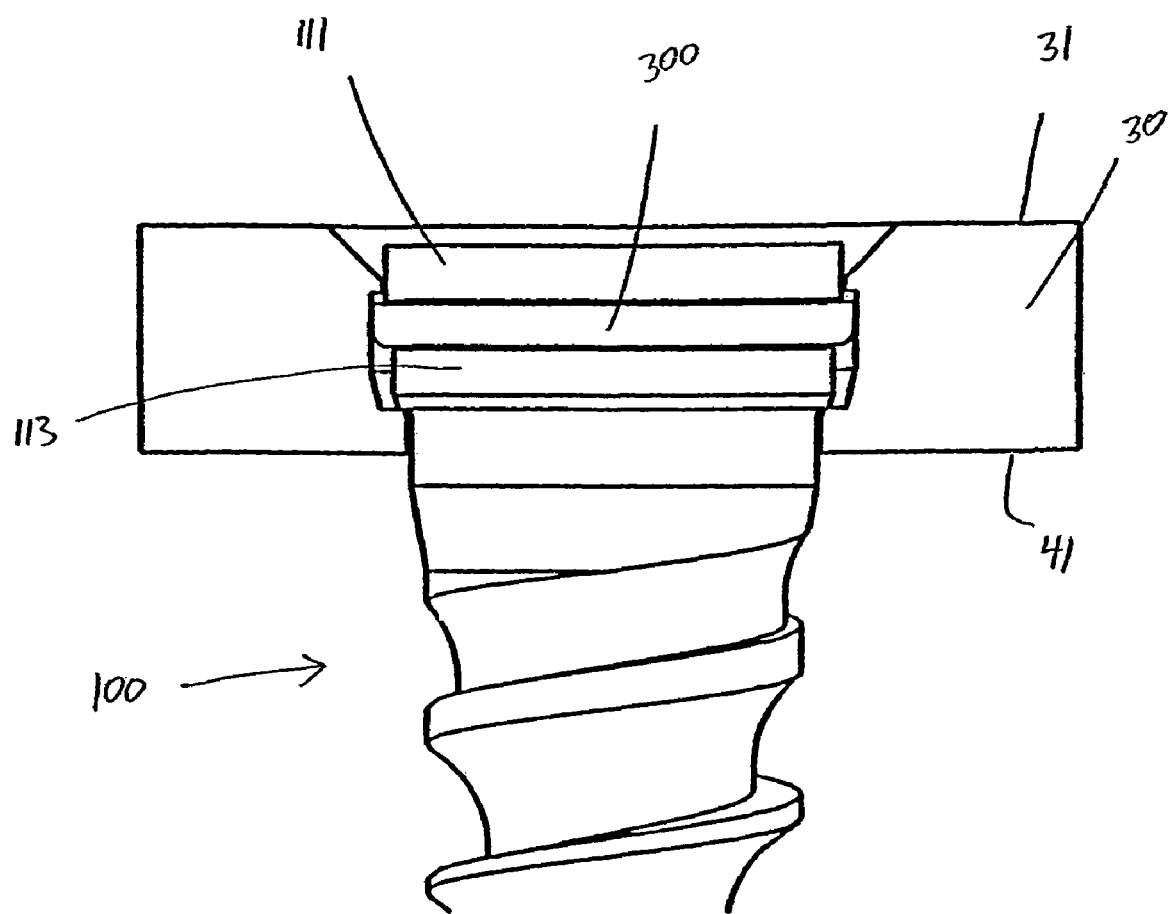
FIG. 18 is a detailed cross-sectional view of a plate through-hole having a fixed screw according to a preferred embodiment of the present invention inserted therein.
Figure 19:
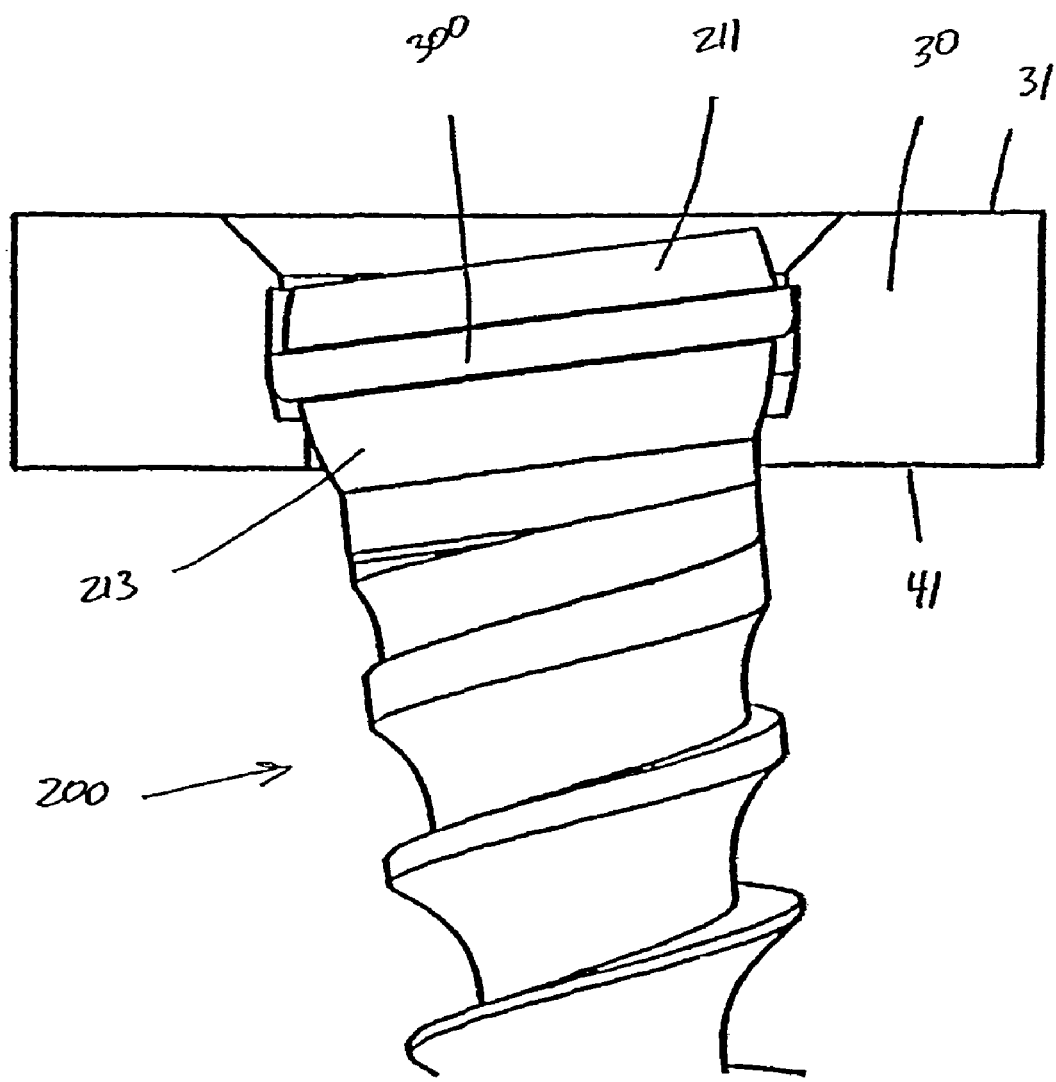
FIG. 19 is a detailed cross-sectional view of a plate through-hole with a variable screw according to a preferred embodiment of the present invention inserted therein after angulation has occurred.

The exit 38 comprises a ramped section 37 at its proximal end adjacent a cylindrical opening 48 at its distal end. The ramp section 37 is provided to keep the locking ring 300 compressed while the variable screw 200 is toggled or angulated within the through-hole 32. Due to the design of the head 210 and shank 220 of the variable screw 200, the ramp 37 allows the longitudinal axis of the variable screw 200 to attain various angles of inclination from the longitudinal axis 33 of the through-hole 32. In particular, when a variable screw 200 is placed within the through-hole 32, the head 210 and shank 220 of the variable screw 200 allows the outer diameter 304 of the locking ring 300 to move along and interact with the surface of the ramp 37. As this occurs, the ramp 37 provides continual radial compression on the outer diameter 304 of the locking ring 300 so as to maintain positive compressive forces thereon. This maintains a tight and integral connection between the locking variable screw 200 and the plate 30. FIG. 19 shows how a variable screw 200 is allowed to angulate within the through-hole 32. In particular, it is seen that the spherical surface of the lower region 213 rests on and rotates about the upper surface of the exit 38. Conversely, FIG. 18 shows how a fixed screw 100 is prevented from angulation in the same through-hole 32 as a result of the size and shape of the head 110 and shank 120 of the fixed screw 100. In particular, it is seen that the shoulder 121 of the shank 120 fits within the exit 38 and has no room for movement. As a result, the fixed screw 100 cannot angulate about the longitudinal axis 31 of the through-hole 32.

As with the screw 10 and locking ring 300, the plate 30 may be made from various materials including metallic and non-metallic. In the preferred embodiment relating to cervical implant systems, the preferred material is implant grade titanium (Ti-6Al-4V), per ASTM F-136.

Figure 23:
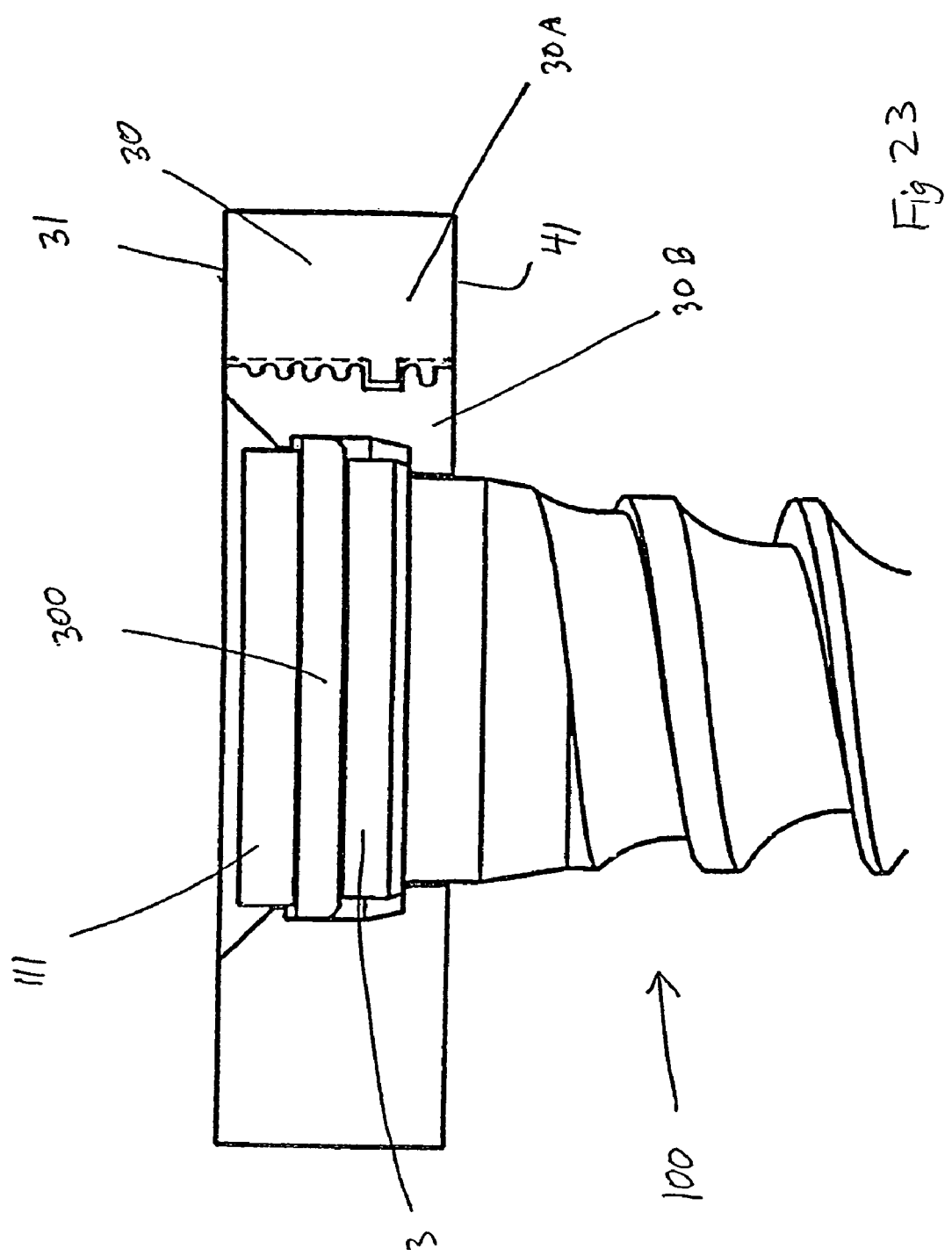
FIG. 23 is a detailed cross-sectional view of an alternative embodiment of a plate having an insert coupled with the plate, wherein the insert contains a through-hole according to the present invention.

FIG. 23 shows an alternative embodiment of the plate 30 enables the use of non-metallic'material for the plate and the use of a metallic screw 10. Presently, the use of a metallic screw against a non-metallic plate is disfavored. One material can create destruction or wear debris in the other material. For instance, a titanium screw may shear a particle off from a nonmetallic plate. This is undesirable for many reasons, including the fact that the Food and Drug Administration has raised concerns about the deleterious effects of wear debris associated with implants. In the alternative embodiment, the plate 30A has an insert 30B molded therein. In this embodiment, the plate 30A is made of inert material, such as a carbon composite, and the insert 30B is made of any of various appropriate metals, such as titanium, and molded into the plate 30A. The use of the insert 30B enables the same material—titanium in the preferred alternative embodiment—to be used for the fastener 10 and for the area within the through-hole 32 which contacts the fastener 10. The use of a separate insert 30B provides great versatility. Many different configurations are possible for the plate 30A and the insert 30B. In addition, the use of a separate insert 30B provides the ability to configure the through-hole 32 in a variety of ways, not just limited to the structure of the through-hole 32 described herein.

The insert 30B may be placed within the plate 30A using in a variety of ways, including the use of threaded means, adhesives, molding techniques, ultrasonic welding, heat staking, compression fit techniques, and so forth. In the preferred alternative embodiment, the insert 30B is fastened to the plate 30A during the molding process in the forming of the plate 30A.

Having described the fixed screw 100, the locking ring 300, the variable screw 200, and the plate 30, it is now helpful to describe how the locking screw 10 and plate 30 of the present invention work in operation. As described above, the first step is to install the locking ring 300 on a screw (either a fixed screw 100 with the use of the sleeve 150, or a variable screw 200), making sure that the flat trailing surface 307 of the locking ring 300 is facing the proximal end of the screw 10. Once the locking ring 300 has been installed on the screw 10, the locking screw 10 is ready to be installed into the plate 30. Ordinarily, in cervical fixation techniques, the area to be instrumented has already been dissected and prepared, and the plate size and shape has already been selected.

The surgeon may pre-drill or pre-awl a hole in the bone to be instrumented. Additionally, the surgeon may tap the drilled or awled hole in order to better accept the threads 131 of the screw 10.

Using a driving instrument that cooperates with the internal cavity sections 115, 116 in the head 110 of the screw 10, the surgeon secures the locking screw 10 to the driving instrument by, preferably, inserting the driving instrument into the first cavity section 115 and engaging the external threads of the driving device with the internal threads of the second cavity section 116 in the head 110 of the screw 10. Having done this, the surgeon then inserts the locking screw 10 into a desired through-hole 32 in a plate 30 located at the region desired to be instrumented. The surgeon installs the screw by engaging the tip 134 of the screw 10 with a portion of bone, and begins rotatably threading the screw 10 into the bone. As the surgeon rotatably threads the screw 10 into the bone, the screw 10 progressively enters the bone. The surgeon continues this until the chamfer 309 on the leading surface 308 of the locking ring 300 begins interacting with the lead chamfer 74 of the entrance 34 of the through-hole 32. Upon further insertion, the surgeon is able to continually radially compress the locking ring 300 as it passes through the collar section 35.

Once the locking ring 300 has exited the collar section 35, it expands to fit the diameter of the undercut 36 of the through-hole 32. The surgeon can insert any number of fixed or variable screws 100, 200 in this manner, thereby securely fastening a bone implant to one or more bone segments. Once the locking ring 300 expands to fit the internal diameter of the undercut 36, the screw 10 is thereby effectively and securely retained in the plate 30. Because the trailing surface 307 of the locking ring 300 is flat, and because the force required to remove the screw 10 from the through-hole 32 is relatively large as a result of the lip 46, the locking screw system prevents screw backout or migration. Conversely, because the leading surface 308 is radiused and because of the presence of the lead chamfer 74, the force required to install the screw 10 into the bone is relatively minimal and requires only a low torque on the part of the surgeon. This significantly reduces the possibility that the surgeon will strip the threads 131 in poor quality bone.

It should be appreciated that once the locking ring 300 is retained in the plate 30, the surgeon still can further turn the screw 10 to continue drawing the plate 30 up against the bone segments. That is, merely retaining the screw 10 in the plate 30 does not prevent the screw 10 from being further tightened or further threaded by the surgeon.

While there has been described and illustrated particular embodiments of a fixed and variable locking fixation assembly, it will be apparent to those skilled in the art that variations and modifications are possible without deviating from the broad spirit and principle of the present invention, which shall be limited solely by the scope of the claims appended hereto.

The invention claimed is:

1. A locking fastener having a proximal end and a distal end terminating in a tip, comprising:
   a) a head disposed at said proximal end having an upper region, a groove adjacent said upper region, and a lower region adjacent said groove; wherein said upper region has a first diameter at said proximal end and a second diameter adjacent said groove and wherein said lower region has a third diameter adjacent said groove and a fourth diameter at a distal end of said lower region;
   b) a shank adjacent said head, wherein said shank further comprises a shoulder adjacent said lower region of said head;
   c) a threaded section adjacent said shank
   d) a locking ring having an outer diameter and an inner diameter and a leading surface having a leading diameter associated therewith and a trailing surface having a trailing diameter associated therewith, wherein said leading surface further comprises a chamfer or fillet, and wherein said locking ring resides within said groove of said head; and
   e) wherein said leading diameter is less than said trailing diameter, and said trailing diameter is substantially equal to said outer diameter.

2. The locking fastener of claim 1 wherein said locking ring further comprises a split ring having an annular cylindrical shape.

3. The locking fastener of claim 1 wherein said groove has a diameter less than said second diameter of said upper region of said head and less than said third diameter of said lower region of said head.

4. The locking fastener of claim 1 wherein said outer diameter of said locking ring is greater than said first diameter and said second diameter of said upper region of said head and greater than said third diameter and said fourth diameter of said lower region of said head.

5. The locking fastener of claim 1 wherein at a resting position said inner diameter of said locking ring is less than said second diameter of said upper region of said head and less than said third diameter of said lower region of said head.

6. The locking fastener of claim 5 wherein said locking ring is elastically deformable from said resting position to a second position wherein said inner diameter of said locking ring is equal to said third diameter of said lower region of said head.

7. The locking fastener of claim 6 wherein said elastic deformation is provided by a break in a circumference of said locking ring.

8. The locking fastener of claim 1 wherein said first diameter of said upper region of said head is equal to said second diameter of said upper region of said head, and wherein said third diameter of said lower region of said head is equal to said fourth diameter of said lower region of said head.

9. The locking fastener of claim 8 wherein said upper region of said head and said lower region of said head each comprise an outer surface that is cylindrical.

10. The locking fastener of claim 9 wherein said shank mates with a through-hole in a plate member such that said locking fastener cannot angulate about a longitudinal axis through said through-hole.

11. The locking fastener of claim 1 wherein said first diameter of said upper region of said head is less than said second diameter of said upper region of said head, and wherein said third diameter of said lower region of said head is greater than said fourth diameter of said lower region of said head.

12. The locking fastener of claim 11 wherein said upper region of said head and said lower region of said head each comprise an outer surface that is a portion of a sphere.

13. The locking fastener of claim 12 wherein said shank mates with a portion of a through-hole in a plate such that said locking fastener can angulate about a longitudinal axis of said through-hole.

14. A locking fastener, comprising:
a screw, wherein said screw comprises a proximal screw head and a threaded section distal of said screw head,
said screw head comprising a groove therein, said groove having a groove innermost axial dimension; and
a retainer within said groove, said retainer having a retainer maximum axial dimension, wherein said retainer maximum axial dimension is less than said groove innermost axial dimension; and
said retainer comprising a leading end having a leading diameter and a trailing end having a trailing diameter, wherein said trailing diameter is greater than said leading diameter.

15. The locking fastener of claim 14, wherein said retainer is capable of elastically deforming between a more-outward configuration in which said retainer extends beyond an envelope of said screw head, and a more-inward configuration that is smaller than said more-outward configuration.

16. The locking fastener of claim 14, wherein said retainer is able to be deformed, while remaining within its elastic limit, to a size such that a maximum diameter of said screw head on a side facing said threaded section can pass through said retainer.

17. The locking fastener of claim 14, wherein said screw head comprises a substantially spherical shape on a surface facing said threaded section.

18. The locking fastener of claim 14, wherein said screw head comprises a first cavity within said screw head, and, adjacent said first cavity distal of said first cavity, a second cavity having internal threads.

19. The locking fastener of claim 14, wherein said retainer comprises a split ring.

20. The locking fastener of claim 14, wherein said groove is bounded by two walls which are substantially parallel with each other.

21. The locking fastener of claim 14, wherein said retainer is substantially flat.

22. A locking fastener, comprising:
a screw, wherein said screw comprises a proximal screw head and a threaded section distal of said screw head,
said screw head comprising a groove therein, wherein said groove has a pair of substantially parallel sides; and
a retainer at least partially within said groove; and
said retainer comprising a leading end having a leading diameter and a trailing end having a trailing diameter, wherein said trailing diameter is greater than said leading diameter.

23. The locking fastener of claim 22, wherein a maximum axial dimension of said retainer is less than a dimension between said substantially parallel sides of said groove.

24. The locking fastener of claim 23, wherein said retainer has substantially parallel sides.

25. The locking fastener of claim 22, wherein said screw head further comprises a substantially spherical shape on a surface facing said threaded section.

26. The locking fastener of claim 22, wherein said retainer comprises a split ring.

27. A locking fastener comprising:
a screw, wherein said screw comprises a proximal screw head and a threaded section distal of said screw head,
said screw head comprising a groove therein; and
a retainer at least partially within said groove,
wherein said retainer has an edge comprising a flat surface in a portion thereof and comprises a chamfer or rounding adjoining said flat surface.

28. The locking fastener of claim 27, wherein said flat surface of said retainer is in a plane that is at least approximately perpendicular to an axis of said screw.

29. The locking fastener of claim 27, wherein said edge is chamfered having a chamfer angle suitable to deflect said retainer inward as said locking fastener slides past a stationary surface.

30. The locking fastener of claim 27, wherein said screw head comprises a substantially spherical shape on a surface facing said threaded section.

31. The locking fastener of claim 27, wherein said retainer comprises a split ring.

32. A locking fastener, comprising:
a screw, wherein said screw comprises a proximal screw head and a threaded section distal of said screw head,
said screw head comprising a groove therein, wherein said groove has two sides that are flat and lie in planes substantially perpendicular to a longitudinal axis of said screw; and
a retainer at least partially within said groove; and
said retainer comprising a leading end having a leading diameter and a trailing end having a trailing diameter, wherein said trailing diameter is greater than said leading diameter.

* * * * *